(12) United States Patent
Abbaszadeh

(10) Patent No.: US 9,872,524 B2
(45) Date of Patent: Jan. 23, 2018

(54) PUMPING/NURSING BRA

(71) Applicant: Simple Wishes LLC, Sacramento, CA (US)

(72) Inventor: Debra Abbaszadeh, Sacramento, CA (US)

(73) Assignee: Simple Wishes LLC, Sacramento, CA (US)

( * ) Notice: Subject to any disclaimer, the term of this patent is extended or adjusted under 35 U.S.C. 154(b) by 497 days.

(21) Appl. No.: 14/172,826

(22) Filed: Feb. 4, 2014

(65) Prior Publication Data

US 2014/0364036 A1 Dec. 11, 2014

Related U.S. Application Data

(63) Continuation-in-part of application No. 14/172,812, filed on Feb. 4, 2014, now abandoned.

(60) Provisional application No. 61/832,592, filed on Jun. 7, 2013.

(51) Int. Cl.
*A41C 3/04* (2006.01)
*A61M 1/06* (2006.01)

(52) U.S. Cl.
CPC .................. *A41C 3/04* (2013.01); *A61M 1/06* (2013.01); *A61M 1/062* (2014.02)

(58) Field of Classification Search
CPC ........... A41C 3/00; A41C 3/04; A41C 3/0028; A41C 3/0021
USPC .............................. 450/36, 86; 2/104; 604/74
See application file for complete search history.

(56) References Cited

U.S. PATENT DOCUMENTS

| | | | |
|---|---|---|---|
| 623,413 | A | 4/1899 | Murray |
| 2,305,051 | A | 11/1940 | Witkower |
| 2,436,430 | A | 2/1948 | Hart |
| 2,492,862 | A | 12/1949 | Harvey |
| 2,522,010 | A | 9/1950 | Woodruff |
| 2,585,338 | A | 2/1952 | Meares |
| 2,613,355 | A | 10/1952 | Coleman |
| 2,679,048 | A | 5/1954 | Alberts |

(Continued)

FOREIGN PATENT DOCUMENTS

| | | |
|---|---|---|
| CN | 201479956 U | 5/2010 |
| EP | 2810573 | 8/2016 |

(Continued)

OTHER PUBLICATIONS

EP Application No. 14171552.4, Extended Search Report dated Sep. 9, 2014, 6 pages.

(Continued)

*Primary Examiner* — Gloria Hale

(57) ABSTRACT

Embodiments for garments are provided with an inner panel having at least one covering for a wearer's breast, the at least one covering having a first layer of material that overlaps a second layer of material, the first and the second layers of material are fastened together to provide an opening between the overlapping layers, and the at least one covering provides support during milk expression for at least one of the wearer's breast and a portion of a breast pump body inserted through the opening, and an exterior front surface having a first panel of material that overlaps at least a portion of the second of panel of material, the first and the second panels able to be moved to expose the at least one covering of the inner panel.

24 Claims, 26 Drawing Sheets

(56) References Cited

U.S. PATENT DOCUMENTS

| | | | |
|---|---|---|---|
| 3,002,515 A | 10/1961 | Glogover | |
| 4,335,728 A | 6/1982 | Fildan | |
| 4,640,287 A | 2/1987 | Anderson et al. | |
| 4,648,404 A | 3/1987 | Clark | |
| 4,878,879 A | 11/1989 | Kunstadter | |
| 5,341,514 A | 8/1994 | Dale | |
| 5,380,238 A | 1/1995 | Crew-Gee | |
| 5,514,166 A | 5/1996 | Silver et al. | |
| 5,575,768 A | 11/1996 | Lockridge et al. | |
| 5,616,125 A | 4/1997 | Jelks | |
| 6,004,186 A | 12/1999 | Penny | |
| 6,027,396 A | 2/2000 | Yochar | |
| 6,227,936 B1 | 5/2001 | Mendoza | |
| 6,247,996 B1 | 6/2001 | Fields | |
| 6,319,092 B1 | 11/2001 | Leyhe et al. | |
| 6,438,758 B1 | 8/2002 | Burkard et al. | |
| 6,440,100 B1 | 8/2002 | Prentiss | |
| 6,705,920 B1 | 3/2004 | Engel | |
| 6,866,558 B2 * | 3/2005 | Luciano | A41C 3/04 450/36 |
| 6,887,217 B1 | 5/2005 | Logan | |
| 6,974,361 B2 * | 12/2005 | Cravaack | A41C 3/04 450/36 |
| 7,232,359 B1 | 6/2007 | Richardson | |
| 949,414 A1 | 2/2010 | Cunningham | |
| 8,192,247 B2 | 6/2012 | Abbaszadeh | |
| 8,323,070 B2 * | 12/2012 | Abbaszadeh | A41C 3/04 2/104 |
| 9,167,855 B2 | 10/2015 | Abbaszadeh | |
| 2003/0027491 A1 | 2/2003 | Cravaack et al. | |
| 2003/0167037 A1 * | 9/2003 | Fialkoff | A41C 3/04 604/74 |
| 2003/0191433 A1 | 10/2003 | Prentiss | |
| 2004/0016039 A1 | 1/2004 | Caprio | |
| 2006/0211336 A1 * | 9/2006 | Brigham | A61M 1/06 450/86 |
| 2007/0161330 A1 | 7/2007 | Whitehead et al. | |
| 2008/0039781 A1 | 2/2008 | Bjorge | |
| 2008/0146118 A1 | 6/2008 | Solberg et al. | |
| 2008/0262420 A1 | 10/2008 | Dao et al. | |
| 2009/0286452 A1 | 11/2009 | Grayson | |
| 2011/0092134 A1 | 4/2011 | Alva | |
| 2011/0237156 A1 | 9/2011 | Boonen et al. | |
| 2011/0314587 A1 | 12/2011 | Ritchie | |
| 2012/0184179 A1 | 7/2012 | Blitz | |
| 2014/0087625 A1 | 3/2014 | Ironi | |
| 2014/0273737 A1 | 9/2014 | Cortese et al. | |
| 2014/0364035 A1 | 12/2014 | Abbaszadeh | |
| 2016/0015092 A1 | 1/2016 | Abbaszadeh | |

FOREIGN PATENT DOCUMENTS

| | | |
|---|---|---|
| FR | 881406 A | 4/1943 |
| FR | 919893 A | 3/1947 |
| WO | 2007/053073 A1 | 5/2007 |
| WO | WO 2008/005713 | 1/2008 |
| WO | WO 2010/080122 | 7/2010 |
| WO | WO 2011/135092 | 11/2011 |

OTHER PUBLICATIONS

EP Application No. 14171556.5, Extended Search Report dated Sep. 10, 2014, 5 pages.

"Pump Up the Band Hands Free Nursing Bra", Nursing Bra Express (Mar. 2, 2013), retrieved from WayBack Machine: http://www.nursingbraexpress.com/nursing-bras/pump-band-hands-free-nursing-bra.

International Search Report and Written Opinion for International Application No. PCT/US2009/006618, dated Mar. 8, 2010, 9 pages.

Office Action for U.S. Appl. No. 12/453,073, dated Sep. 23, 2011, 11 pages.

Office Action for U.S. Appl. No. 12/585,829, dated Aug. 24, 2011, 10 pages.

Office Action for U.S. Appl. No. 13/692,204, dated Oct. 1, 2014, 9 pages.

Office Action for U.S. Appl. No. 13/692,204, dated Jul. 3, 2013, 6 pages.

Office Action for U.S. Appl. No. 13/692,204, dated Apr. 8, 2014, 6 pages.

Office Action for U.S. Appl. No. 14/867,979, dated Nov. 5, 2015, 8 pages.

Office Action for U.S. Appl. No. 14/867,979, dated Apr. 4, 2016, 6 pages.

Office Action for European Application No. 14171552.4, dated Dec. 3, 2015, 4 pages.

Office Action for U.S. Appl. No. 14/172,812, dated Jun. 16, 2016, 8 pages.

Office Action for Chinese Application No. 201410077245.4, dated Dec. 7, 2016, 31 pages.

European Search Report for European Application No. 16179769.1, dated Feb. 10, 2017, 8 pages.

International Search Report and Written Opinion for International Application No. PCT/US2016/043326, dated Nov. 28, 2016, 20 pages.

* cited by examiner

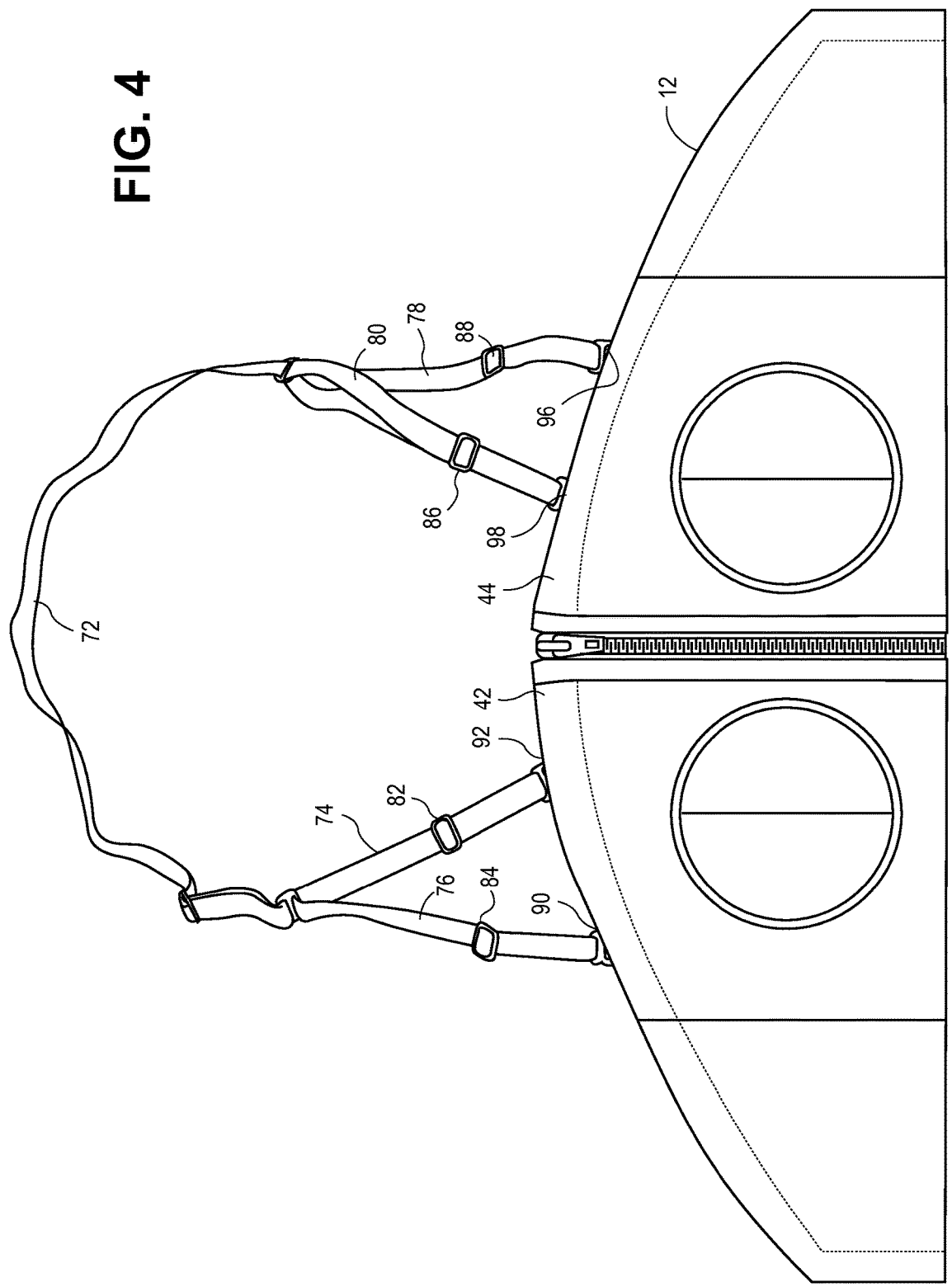

PUMPING/NURSING BRA

CROSS REFERENCE TO RELATED APPLICATIONS

This application is (i) a NONPROVISIONAL of, claims priority to, and incorporates by reference in its entirety U.S. Provisional Application No. 61/832,592, filed on Jun. 7, 2013, and (ii) is also a Continuation in Part of, claims priority to, and incorporates by reference in its entirety U.S. Non-Provisional application Ser. No. 14/172,812, entitled "Pumping/Nursing Bra", filed Feb. 4, 2014, which also claims priority to U.S. Provisional Application No. 61/832, 592, filed on Jun. 7, 2013.

FIELD OF THE INVENTION

Various embodiments relate to a garment worn to provide support while the wearer is pumping breast milk.

BACKGROUND

A breast pump may be used to express milk from a breast. Implementations of breast pumps have a pump body to express the milk and a milk container to receive the milk. The pump body of a breast pump may have a breast shield or a flange having a funnel shape with a cup portion that fits over at least a portion of a breast.

A let-down cushion or let-down massage cushion of a breast pump may fit between a breast shield or a flange of a pump body of the breast pump and a breast. The let-down cushion may fit within the breast shield or flange and have an edge that folds over an edge of the breast shield or the flange of the pump body. The let-down cushion may flex in and out to massage the areola of a breast to help stimulate milk flow. A seal may be formed between the let-down cushion and a breast to create suction and encourage breast milk expression.

To use a breast pump, a user manually holds the breast flange, shield, or pump body over a breast. While using the breast pump, the wearer is not able to use their hands for any other tasks. It may be desirable to express milk from both breasts simultaneously, but doing so, requires the user to hold both breast pump bodies against oneself and is both awkward and does not allow the user to do any other tasks. As such, garments that assist in supporting the breast pump body for milk expression are needed to allow a wearer to use their hands for other tasks during milk expression with a breast pump.

SUMMARY OF THE INVENTION

Embodiments for garments are provided with an inner panel having at least one covering for a wearer's breast, the at least one covering having a first layer of material that overlaps a second layer of material, the first and the second layers of material are fastened together to provide an opening between the overlapping layers, and the at least one covering provides support during milk expression for at least one of the wearer's breast and a portion of a breast pump body inserted through the opening, and an exterior front surface having a first panel of material that overlaps at least a portion of the second panel of material, the first and the second panels able to be moved to expose the at least one covering of the inner panel.

BRIEF DESCRIPTION OF THE DRAWINGS

FIG. 4 depicts an exemplary garment in accordance with some embodiments of the invention.

DETAILED DESCRIPTION

Figure 1A:
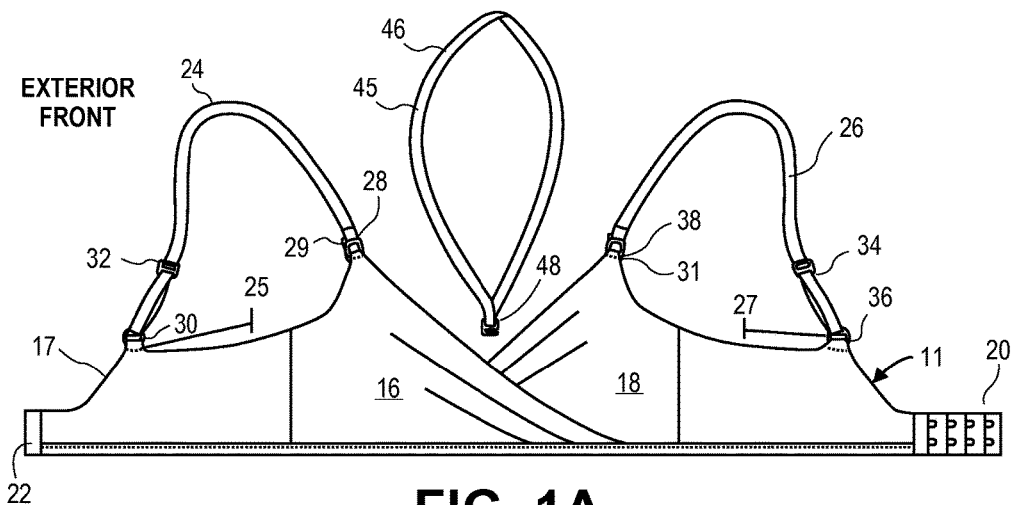
FIG. 1A depicts an exemplary garment in accordance with some embodiments of the invention.

Apparatuses, articles, processes for manufacture, garments, bustiers, breast pumping bras, and nursing bras that provide support to a wearer and/or at least a portion of a breast pump to aid with milk expression using a breast pump are described. For example, a garment, such as a bra, a tank top, or a bustier, may provide support for the weight of a breast pump body, milk container, and/or a wearer's breast, help secure the breast pump body in place, and/or stabilize the breast pump body for milk expression. Various embodiments may provide support to aid with creation of a tight seal between the wearer's breast and at least a portion of a breast pump body for milk expression (e.g., a breast shield and/or a let-down cushion of a breast pump body). The wearer of the garment may be able to pump breast milk without having to manually hold the breast pump body against themselves.

Garments in accordance with some embodiments may have openings formed between overlapping layers of material that are fastened together and/or to panels of the garment to provide openings for access to a wearer's breasts. In particular, the garment may have an inner panel (e.g., a pumping panel) having two openings providing access to the wearer's breasts that are created between respective sets of overlapping layers of material. Each opening is between the corresponding set of overlapping layers of material and the overlapping layers are fastened together to provide the respective opening.

In some embodiments, the garment may have an exterior surface of one or more panels of material that cover the inner panel. When the panels of material and the layers of material that cover an opening are moved, the wearer may be able to insert a portion of the breast pump body through the opening, and the layers of material and/or the panels of material of the garment may aid in supporting the breast pump body and/or the wearer's breast. The materials used for the inner and the exterior panel may be a fabric capable of being stretched to allow for pushing the material out of the way to insert the pump body portion, and the fabric may have some elasticity to then fit snugly under and/or around the pump body portion for support and return to the panels original shape covering the inner panel. In some embodiments, the garment may have elastic edges to prevent the garment from slipping down as well as providing additional support for the wearer's breasts.

Some embodiments may have one or more loops of a material (e.g., elastic, fabric, etc.) attached to the garment. Each loop may be designed to secure a portion of a breast pump in place (e.g., a loop to hook or fit around a breast shield to aid in the support of the breast pump body and milk container for pumping milk).

Some embodiments may have adjustable straps that may be selectively attached to the garment, such as a garment with a top line on the garment with corresponding attachment mechanisms to that found on a strap thereby allowing the strap to be attached thereto. For example, the top line may be a piece of material (e.g., an elastic band) attached to an edge of a panel (e.g., an inner panel) and the corresponding attachment mechanisms may be sewn to the garment with stitching between the elastic band and the fabric of the garment. The one or more attachment mechanisms (e.g., corresponding attachment mechanisms to the attachment mechanisms found on the strap) may be sewn in to the garment for selectively attaching a strap in one of a plurality of positions to support a breast pump body.

By way of further example, a neck strap may extend around the back of the wearer's neck and may be attached to the top line of the garment. The garment (e.g., a top line of a pumping/nursing bra) may have one or more selective attachment mechanisms (e.g., loops or hooks allowing for attachment of the strap to the garment). A plurality of selective attachment mechanisms may be provided on the garment to provide a plurality of positions for the strap. Attachment mechanisms may be hooks that may be selectively attached to a loop (e.g., a fabric, metal, or plastic loop), snaps, buttons and button holes, ribbon ties, lace ties, string ties, and/or any other attachment mechanism that can be selectively attached or detached. For example, a wearer could use a ribbon, lace, heavy string, etc. that could be threaded through a loop on the topline and tied where the two ends join. There may be a single strap and/or multiple straps that extend from one area of the bra to another as opposed to fitting around the neck. For example, a single strap could attach at the front topline, extend over the shoulder and hook at the topline below the underarm or back.

Continuing with the example, the neck strap may have a single hook that can be attached to the garment or a plurality of hooks that may be attached to the garment. The neck strap may ensure that the garment remains in place during breast pumping, particularly when the breast pump bottle becomes heavier as container, used with the breast pump to collect milk, fills with milk. For example, a neck strap may encircle the neck of the wearer and have at least one hook attached to the top line of the garment to ensure that the garment remains in place during the use of a breast pump with at least one of the wearer's breasts. The neck strap may be used with or without shoulder straps of the garment.

In some embodiments, a pocket or a channel may be provided on a shoulder strap that contains and/or houses a cord or a strap with a hook or an attachment piece to connect to another area of the garment. The cord may be elastic to allow for the cord to be stretched and/or the cord may be stored within the pocket or channel rolled up into a coil, so that the cord can be extended and retracted. The cord may also have a slider to lengthen and shorten the strap as needed.

Other objects and advantages of the present invention will become apparent from the following detailed description when viewed in conjunction with the accompanying drawings, which set forth certain embodiments of the invention. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and or use the invention.

FIG. 1A depicts an exemplary garment in accordance with some embodiments of the invention. FIG. 1A illustrates an exterior front surface 17 of a garment 11 (e.g., a pumping/nursing bra). The exterior front surface 17 includes a first panel of a material 16 crossing in front of a second panel of material 18, and both of the panels 16 and 18 provide a cover over the inner panel 19 in a covered state. The material may be any type of fabric capable of being stretched to uncover the inner panel and having elasticity to return to its original shape, and/or fit snugly under and/or around a portion of a breast pump body to provide support. The garment 11 (and garment 12 described below) may be made from nylon/spandex blends, cottons, polyesters, mesh fabrics, sheer fabrics, opaque fabrics, and/or any other materials. In some embodiments, portions of the garment 11 (and garment 12) may be made from fabrics that are sheer, transparent, and/or allow for visibility to the wearer's body (e.g., nylon, mesh, or basket weave). In particular, the sheer fabric of the garment 11 (and garment 12) may allow the wearer to see what areas of her body are irritated from the pumping process, and massage the areas with the sheer, thinner fabric. The panels may consist of one or more pieces of material that are sewn together to form an exterior surface 17. The panel 16 may cross over panel 18 to provide a smooth covering over an inner panel 19. In other embodiments, panel 16 and 18 may be a single panel of material that covers the inner panel. The inner panel 19 may be referred to herein as a pumping panel because the inner panel is formed to provide openings for access to a breast and insertion of a portion of a breast pump body.

In some embodiments, finger holes may be provided on an area of the inner panel to allow for massage to aid in the milk extraction.

Figure 1B:
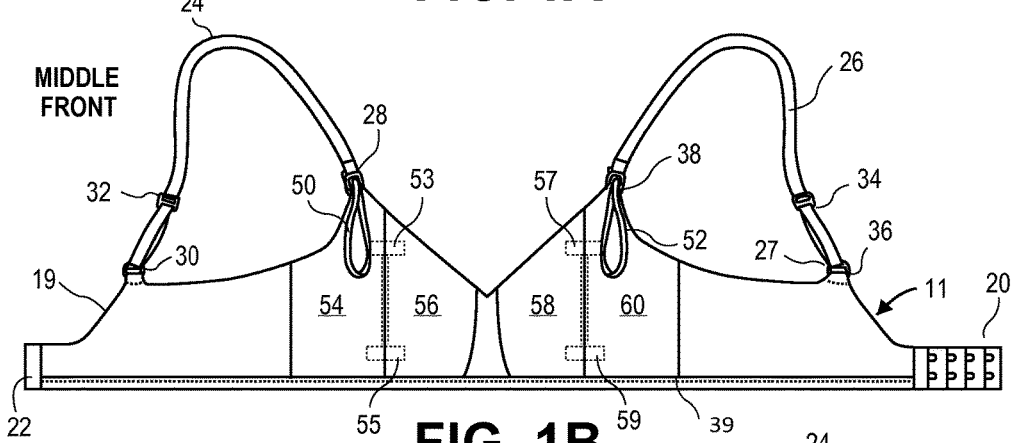
FIG. 1B depicts an exemplary garment in accordance with some embodiments of the invention.

FIG. 1B depicts an exemplary garment in accordance with some embodiments of the invention. FIG. 1B illustrates a front surface of the inner panel 19 (e.g., a pumping panel). The inner panel 19 may be covered by the panels 16 and/or 18 of the exterior front surface 17 in a covered state for the exterior front surface 17, or uncovered and accessible by moving and/or adjusting the panels 16 and/or 18 of the exterior front surface 17 in an uncovered state for the exterior surface 17. The inner panel 19 includes a first set of overlapping layers of material with a first layer of a material 54 and a second layer of a material 56, and a second set of overlapping layers with a third layer of a material 58 and a fourth layer of a material 60. A set of overlapping layers (e.g., layer 54 and layer 56) may be sewn to the garment 11 in such a way to overlap and form an opening and a line that is nearly perpendicular line to the bottom edge 39 of the garment 11, as shown. Those with skill in the art will recognize that an opening may be formed by sewing together layers of material that are at any angle to the bottom edge 39 of a garment, and embodiments are not limited to an opening that is perpendicular to the bottom edge 39.

The material used for the layers of material may be any type of fabric with elasticity to allow the layers to be stretched, moved, and return to their or nearly their original state. A layer of material (e.g., layers 54, 56, 58, or 60) each may be a single piece of material, multiple pieces of material, or a piece of material that has been folded over and sewn to the garment 11 to form a supportive layer of material. The layers of material on the inner panel 19 and panels of the exterior surface 17 may be created from different fabrics and materials.

Overlapping layers 54 and 56 can be moved to uncover, adjusted to separate, and/or allow one of the wearer's breasts to be accessible through the opening between the layers. Overlapping layers 58 and 60 may be likewise separated to uncover, adjusted, and/or allow the other breast of the wearer to be accessible through the opening between the layers. The overlapping layers 54 and 56 may provide support for at least a portion of a breast pump body and/or a milk container when inserted through the opening formed between the overlapping layers. The panels of material 16 and/or 18 in the uncovered state may help to prevent the breast pumps body and/or breast shields from slipping downward from the woman's breast by providing support beneath and/or around the breast pump body inserted through the opening. In some embodiments, the opening may created between overlapping layers by stitching (e.g. bar tack stitching in a rectangular shape at 53 and 55) that fastens the layers of material together and leaves the opening between the stitching of the layers (e.g., bar tack stitching at 53 and 55). In some embodiments, the pump body may sit within the opening, and the may keep the overlapping layers fastened together to fit around and the pump body to keep it in place. Embodiments of the pumping panel 19 may be provided with top rectangular shaped stitching panel 53 and a bottom rectangular shaped stitching panel 55 extending across a portion of the overlapping sections 54, 56 of the pumping panel 19. Similarly a top rectangular stitching panel 57 and a bottom rectangular stitching panel 59 extend across a portion of the overlapping sections 58, 60 of the pump support panel 19. Although a rectangular shaped stitching is described, those with skill in the art will recognize that a variety of shapes and stitching may be fasten the layers together.

Figure 1C:
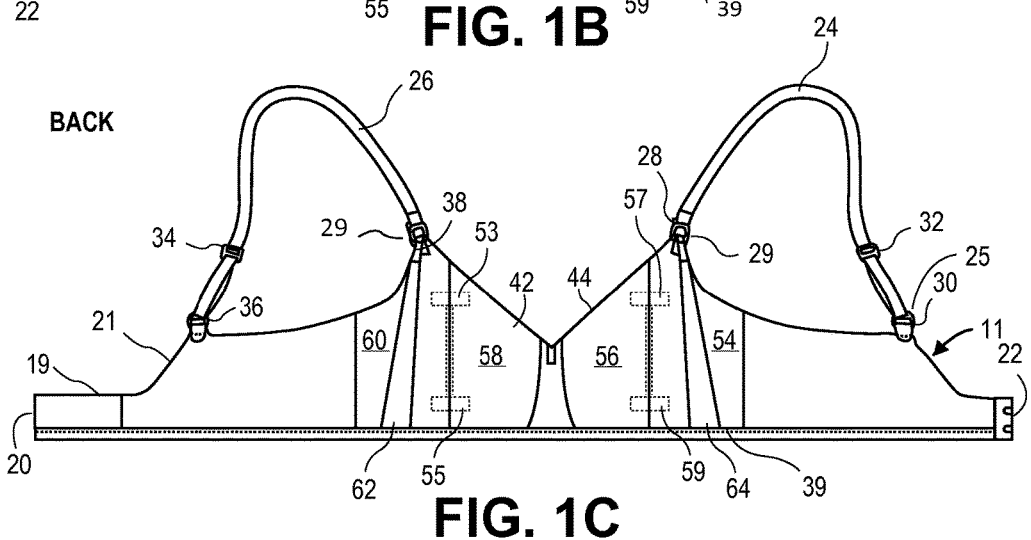
FIG. 1C depicts an exemplary garment in accordance with some embodiments of the invention.

FIG. 1C depicts an exemplary garment in accordance with some embodiments of the invention. FIG. 1C illustrates a rear surface 21 of the inner panel 19. A first shoulder strap 24 is provided at a first garment end 29 of the garment 11 with an attachment mechanism 28. The attachment mechanism 28 may have a first attachment end attached to a first stay end of a first fabric stay 64, and a second attachment end of the attachment mechanism 28 may be attached to a first garment end 29 of the inner panel 19 and one end of the front surface 17 and/or back surface 21 (e.g., panel 16), such as a sewn connection. Those with skill in the art will recognize that the attachment mechanism may be attached to the garment in a number of different ways, such as sewn in to the garment, sewn an elastic band of the garment, slipped onto a strap, and/or any other method for securing the attachment mechanism.

Both first attachment end and second attachment ends of the attachment mechanism 28 (e.g., a hook) are designed to be selectively attached to one another, connecting the first panel 16 to the first fabric stay 64 of the inner panel 19. The first fabric stay 64 may extend down with a second stay end of the first fabric stay 64 attached to the bottom edge 39 of the inner panel 19. A second strap end 25 of the first shoulder strap 24 may be attached to the garment 11 (e.g., a front surface 17, the panel 16, or the back surface 21) by an attachment mechanism 30 (e.g., a hook). Attachment mechanisms may be hooks, double hooks, snaps, buttons, and/or any other attachment mechanism for selective attachment. Alternatively, shoulder straps may cross in the back and first shoulder strap 24 may instead be secured to attachment mechanism 36 and second shoulder strap 26 may be secured to attachment mechanism 30.

A second shoulder strap 26 contains an attachment mechanism 38 (e.g., a hook) having a first attachment end 31 attached to a first stay end of a fabric stay 62. The second stay end of the second fabric stay 62 may be attached to the bottom edge 39 of the garment. A second attachment end of the attachment mechanism 38 is attached to one end of the inner panel 19 and one end of the panel 18. The first and second attachment ends of the attachment mechanism 38 are designed to attach to one another, connecting the second panel 18 to the pumping panel 19. The second shoulder strap 26 contains an attachment mechanism 36 (e.g., a hook member) connected to the garment 11.

A slide member 32 is provided on the first shoulder strap 24 and a slide member 34 is provided on the second shoulder strap 26. The slide members 32 and 34 are used to adjust the length of each of the shoulder straps 24, 26. Adjustable hook and eye closures 20, 22 are used to secure the garment 11 around the wearer's body. Although those with skill in the art will recognize that other closures may be used to secure the garment 11 around the wearer's body, such as a zipper, a tie, VELCRO® closures, snaps, buttons, and/any other closure or attachment mechanism.

In some embodiments, double hook attachment mechanisms may be used as an alternative to the attachment mechanisms (e.g., hooks) 28, 38 shown in FIGS. 1A, 1B, and 1C. Double hook attachment mechanisms 120 will be described further in regards to FIGS. 15 and 16.

As shown in FIG. 1B, a first elastic loop 50 is attached to the first shoulder strap 24, fabric stay 64, and/or i the inner panel 19. Additionally, a second elastic loop 52 is attached to the second shoulder strap 26, fabric stay 62, and/or the inner panel 19. The purpose of the loops 50, 52 is to fit around (e.g., hook) a portion of a breast pump body (e.g., the breast shield) and support the breast pump (e.g., a breast shield). Additional support may be helpful particularly when the breast pump container is filling with milk, as shown and described in further detail with FIG. 12 and FIG. 14. For example, the loops may be an elastic material that is sewn at both ends into the inner panel 19 of the garment 19. Those with skill in the art will recognize that loops may be attached to other parts of a garment 11 and similarly achieve the same purposes.

The loops may be attached to the garment 11 to hold or keep the breast pump body at a particular angle to ensure a seal is formed and/or not broken to allow for successful milk production. In some embodiments, the loop may have a slide or other mechanism to adjust the length of the loop surrounding the portion of the breast pump body. In other embodiments, the loop may have attachment mechanisms to open and close the loop around the breast pump body. The panels of the exterior surface 17 may cover the loops in a covered state.

The embodiment shown in FIG. 1A includes a neck strap 46 that is a single loop 45 joined together (e.g., sewn together) and that has an attachment mechanism 48 (e.g., a hook). The strap 46 may encircle the wearer's neck and then extend down from the wearer's neck toward the garment 11. The attachment mechanism 48 may be attached to a corresponding attachment mechanism (e.g., an opening to receive a hook) provided in a top line 42 and 44 of the garment 11 at a position (e.g., approximately at the center of the inner panel 19). The neck strap 46 may help to keep the garment 11 in place by providing additional stability when the wearer is pumping breast milk, particularly when a breast pump container is full of milk.

Figure 2A:
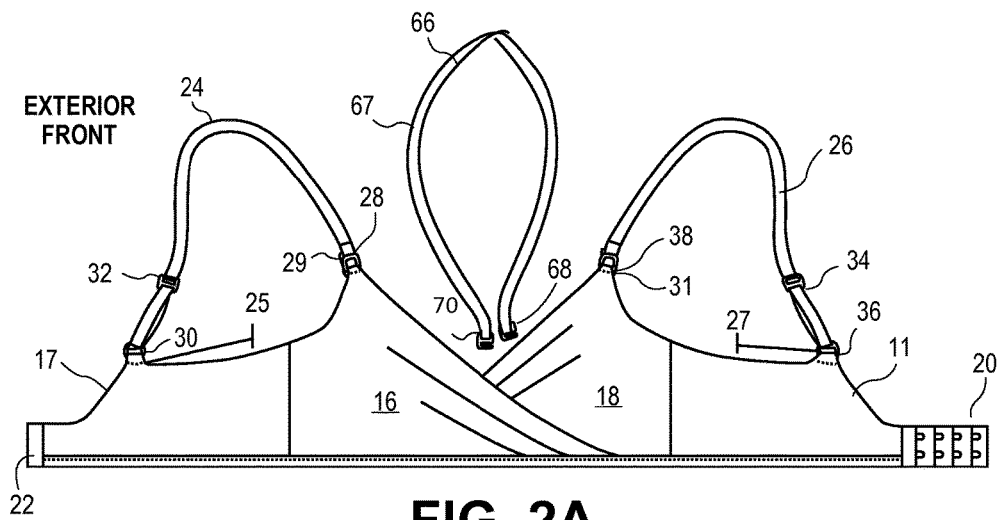
FIG. 2A depicts an exemplary garment in accordance with some embodiments of the invention.
Figure 2B:
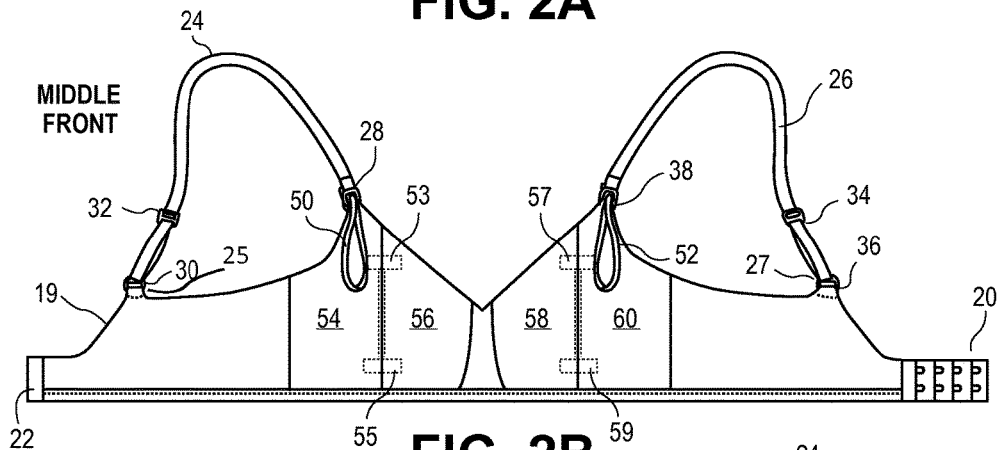
FIG. 2B depicts an exemplary garment in accordance with some embodiments of the invention.
Figure 2C:
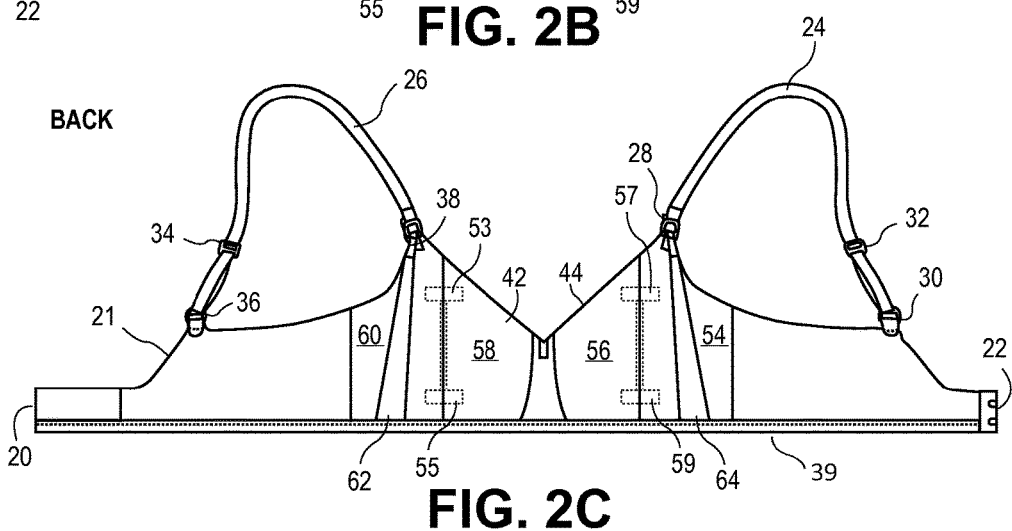
FIG. 2C depicts an exemplary garment in accordance with some embodiments of the invention.

FIGS. 2A, 2E, and 2C illustrate an alternative embodiments that utilize a strap 66 instead of the strap 46. Neck strap 66 may encircle the neck of the wearer with a single loop 67 and may have hooks 68, 70 at each end. Each of the hooks 68, 70 attach to the top line 42 and/or 44 (e.g., close to the center of the pumping panel 19 and/or on either side of the center). For the sake of description, two hook, loop attachments are described. However, those with skill in the art will recognize that a plurality of corresponding loops may be on a top line in a plurality of positions and capable of receiving a hook. Those with skill in the art will recognize that straps 46 and 66 may be secured to the garment 11 in a number of different locations on the top line 42 and/or 44 to provide stability and the positioning near the center is only provided as an example of such a location/position for the strap.

Figure 3A:
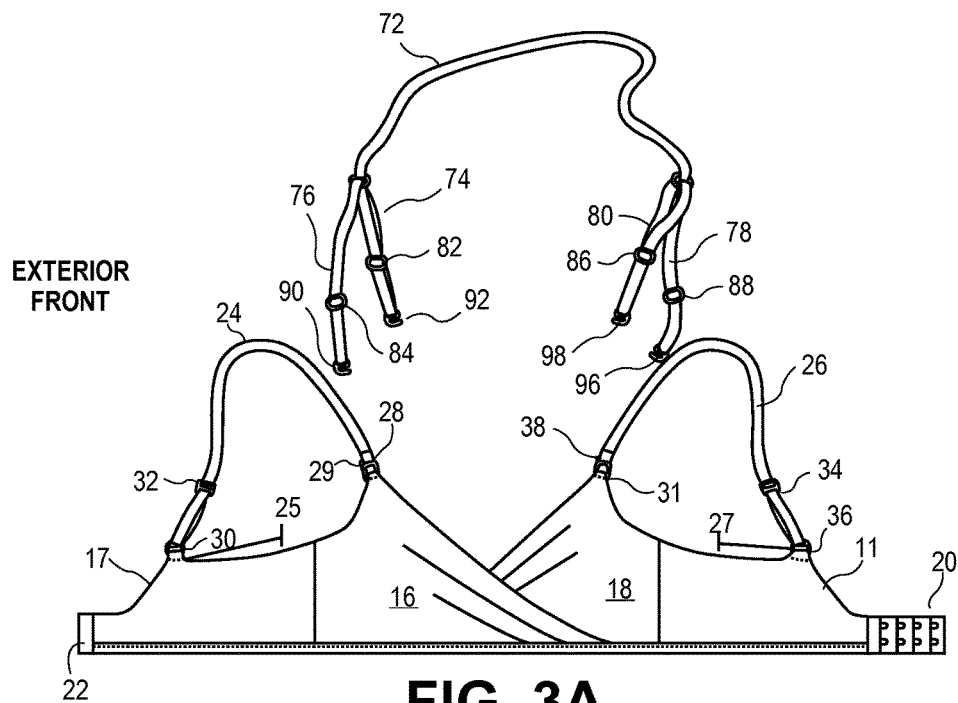
FIG. 3A depicts an exemplary garment in accordance with some embodiments of the invention.
Figure 3B:
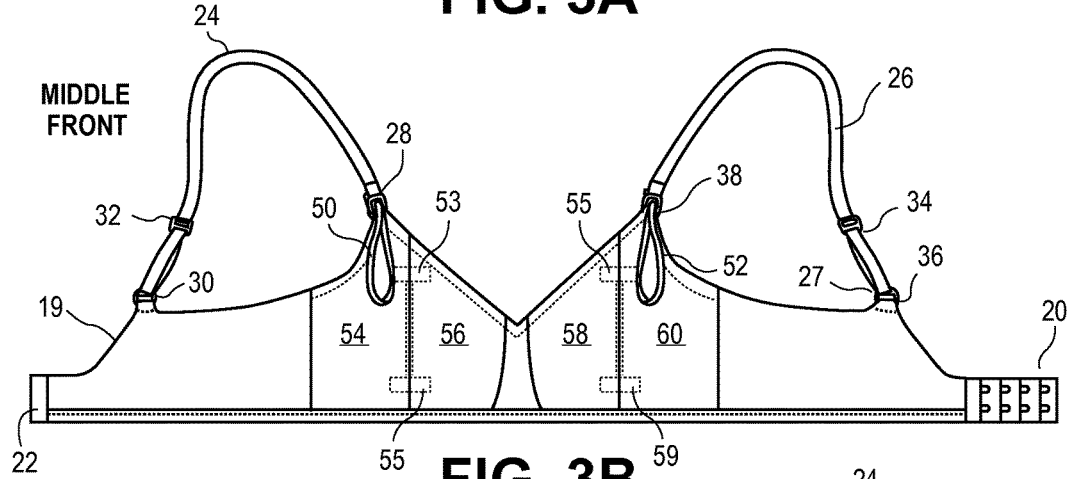
FIG. 3B depicts an exemplary garment in accordance with some embodiments of the invention.
Figure 3C:
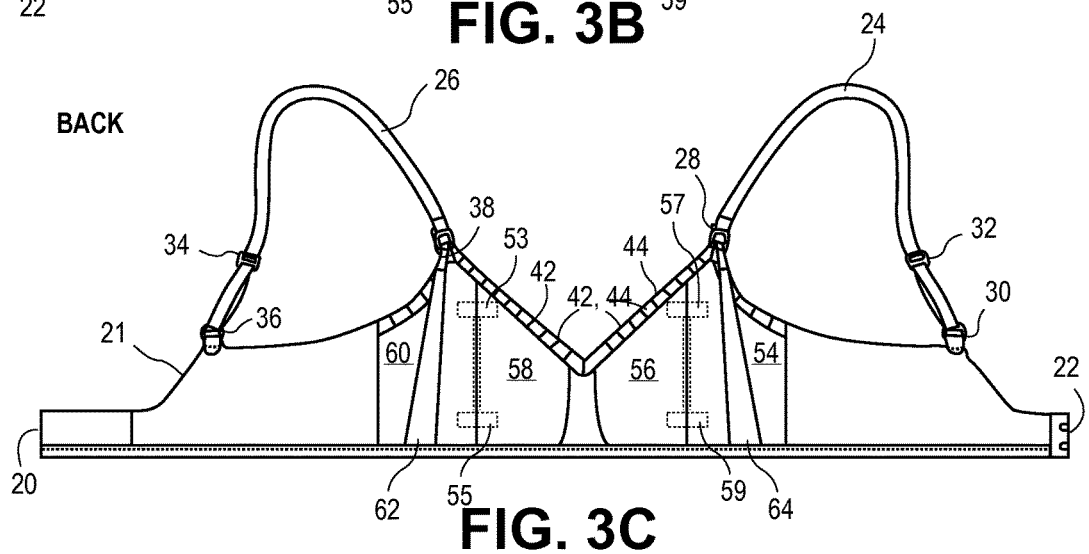
FIG. 3C depicts an exemplary garment in accordance with some embodiments of the invention.

The embodiment shown in FIGS. 3A, 3B, and 3C employs a neck strap 72 in lieu of the straps 46, 66. The strap 72 contains extension sections 74, 76, 78, 80, each of which is provided with hooks 92, 90, 96, 98, respectively. Each of the hooks 90, 92, 96, 98 may be attached to the top line 42, 44. As can be appreciated, an increase in the number of extensions from the strap 72 and hooks secured to the garment 11 may offer greater stability and support for the breast pumps.

FIG. 4 shows an alternative garment that may be used with straps 46, 66, and/or 72. As shown, strap 72 may be attached to the top line 42, 44 of the garment 12. Adjustable slides 82, 84, 86, 88 allow for adjusting the length of the strap 72 to accommodate the wearer. Features of garment 12 are described in U.S. Pat. No. 8,192,247 filed Apr. 29, 2009, U.S. Pat. No. 8,323,070 filed Sep. 25, 2009, and U.S. patent application Ser. No. 13/692,204 filed Dec. 3, 2012, which are each incorporated by reference in their entirety. Garment 12 may have a covering for each opening that has pieces of material attached to a panel. A center panel may be selectively attached to left and right panels of the garment 12 (shown without the center panel).

Figure 5:
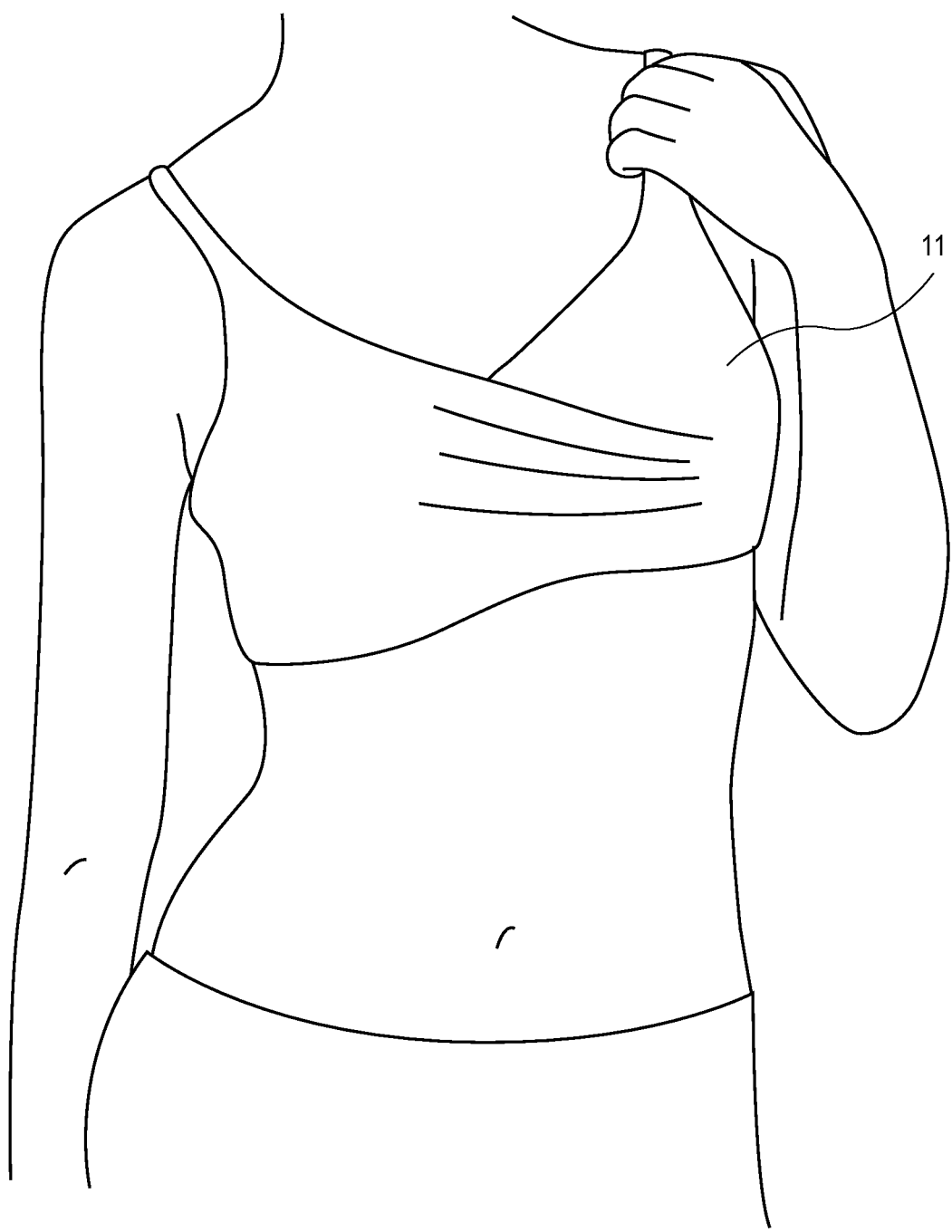
FIG. 5 depicts an exemplary garment in accordance with some embodiments of the invention.
Figure 6:
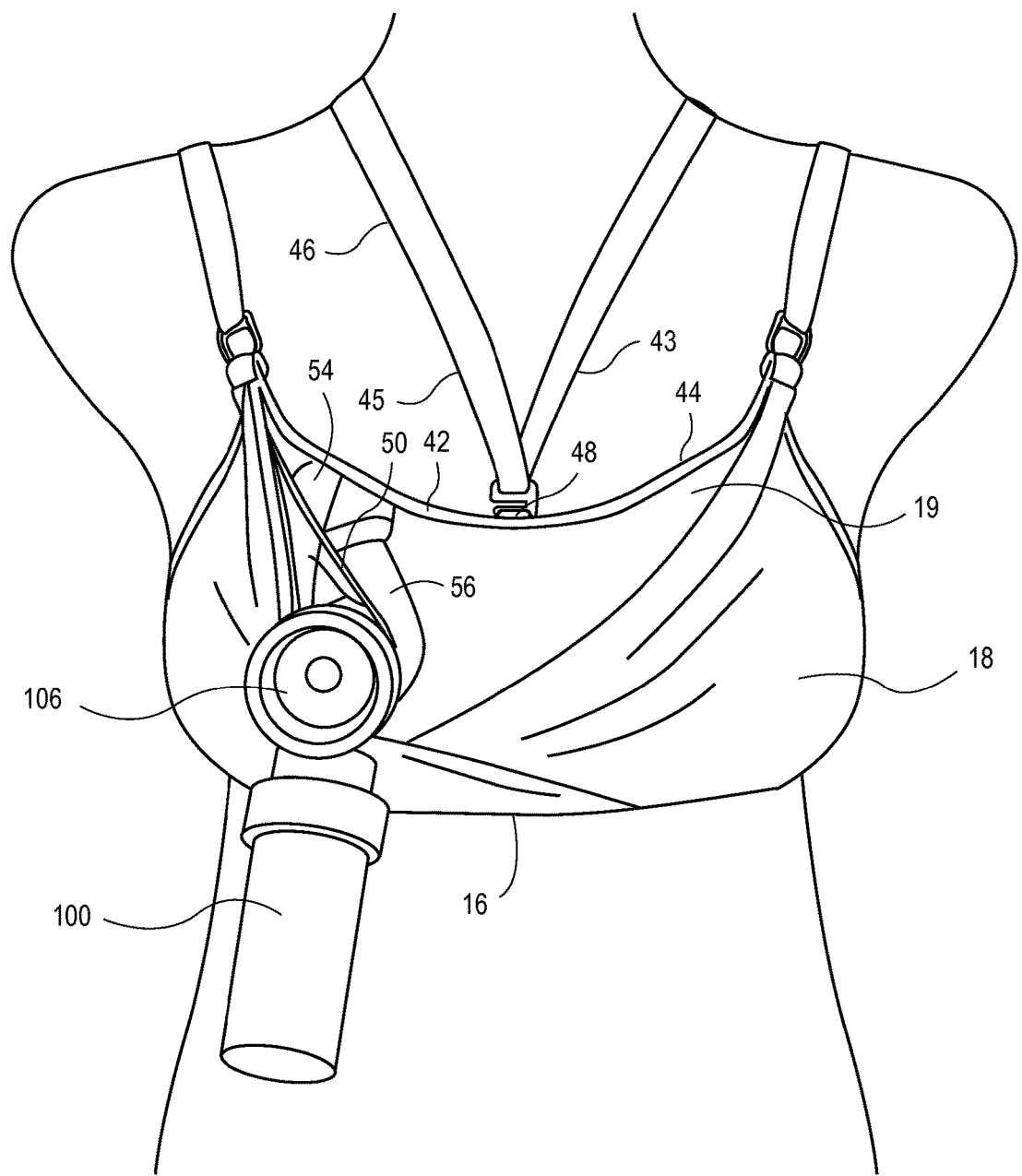
FIG. 6 depicts an exemplary garment in accordance with some embodiments of the invention.

FIGS. 5-13 illustrate the manner in which the garment 11 may be worn and used. The garment 11 may be worn as shown in FIG. 5 in a covered state for the exterior surface 17. As shown in FIG. 6, when breast milk pumping is initiated and/or further support is desired by the wearer, additional straps (e.g., 46, 66, or 72) may fit around the wearer's neck and be attached to the top line 42, 44 of the inner panel 19.

As shown in FIG. 6, the wearer may move the panel 16 slightly downward and/or to the wearer's right, allowing the woman to provide access/expose an opening between panels 54, 56 and to insert a breast shield of a breast pump body 106 between the panels 54, 56 and/or access the wearer's breast. A pumping container 100 may be used to capture expressed milk.

Figure 7:
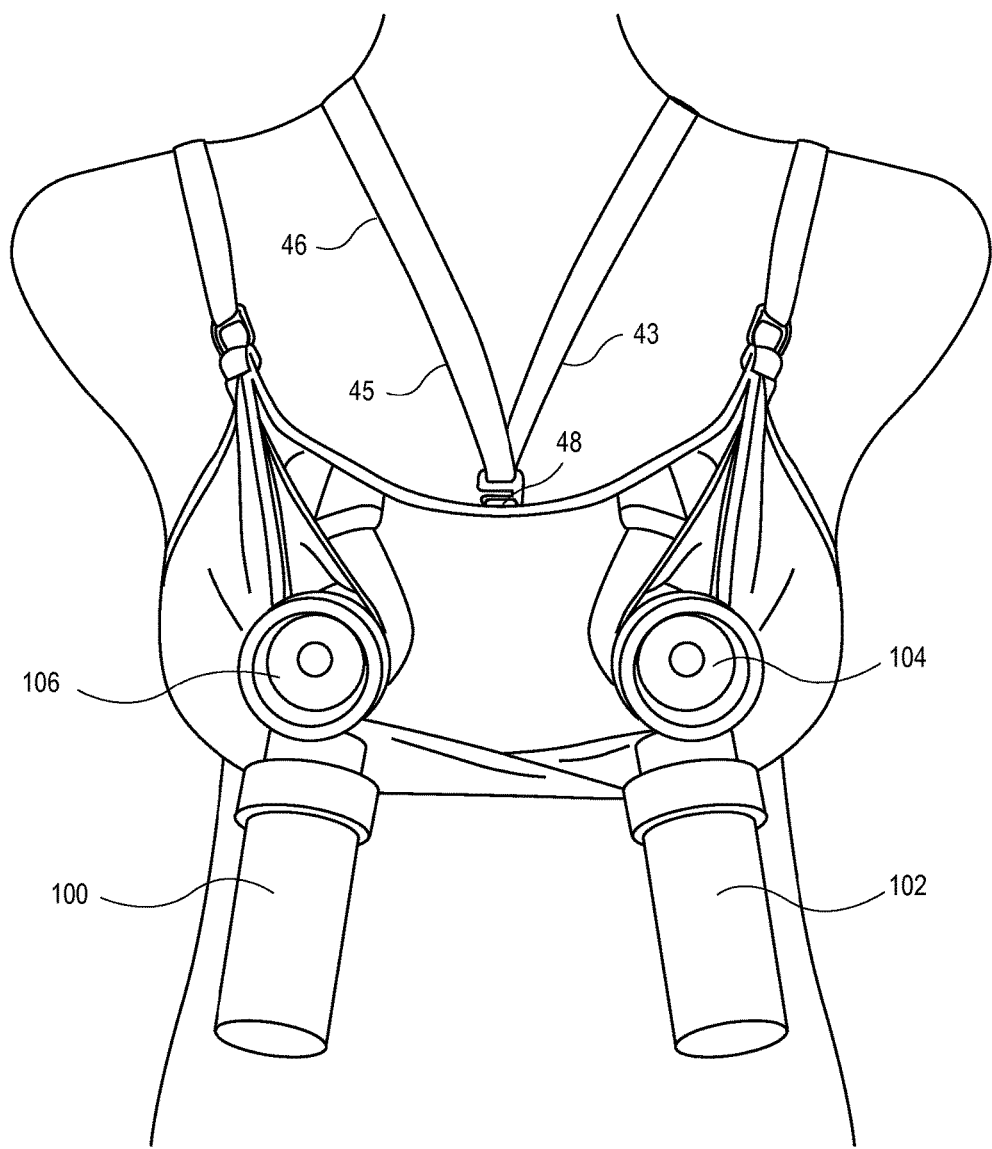
FIG. 7 depicts an exemplary garment in accordance with some embodiments of the invention.

FIG. 7 illustrates the use of two pumping bottles 100, 102 connected to breast pumps with breast shields of breast pump bodies 106, 104 respectively. The breast shields 106 and 104 fit through the openings of the garment 11.

Figure 8:
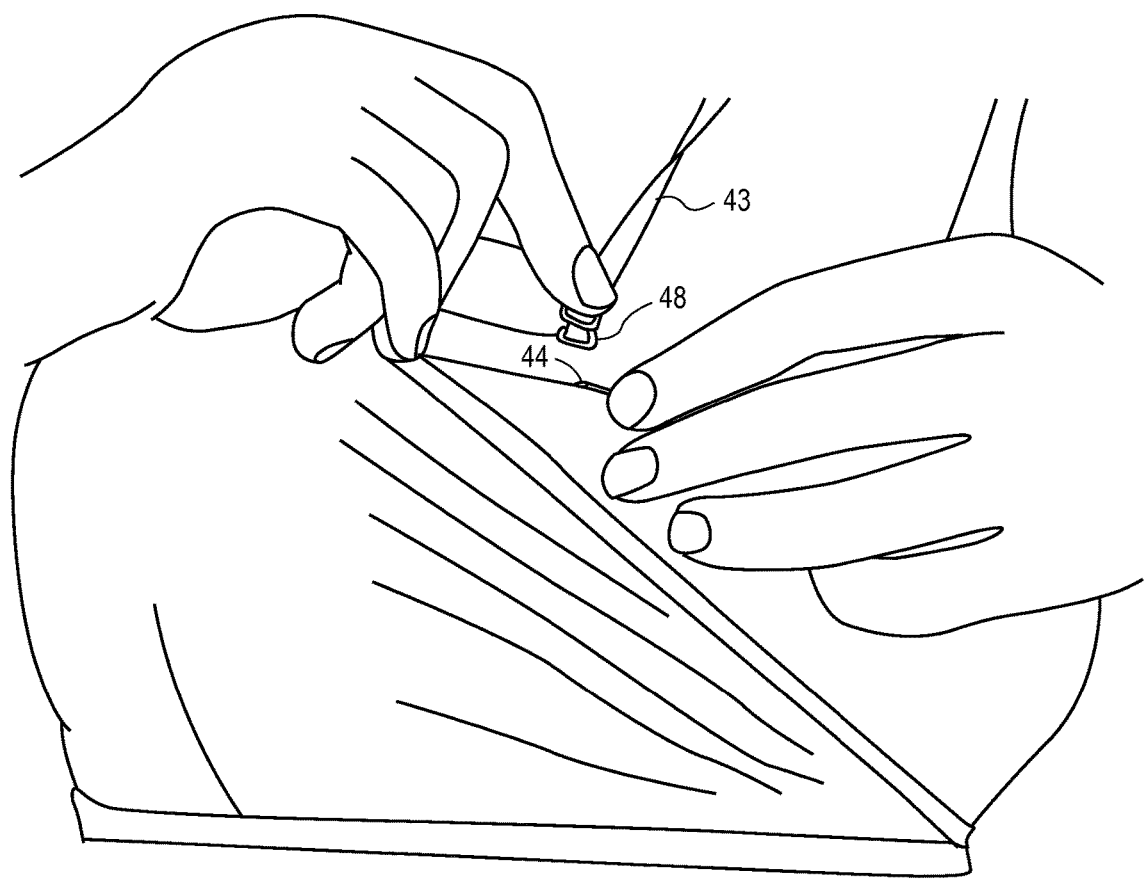
FIG. 8 depicts an exemplary garment in accordance with some embodiments of the invention.

FIG. 8 shows the manner in which the attachment mechanism 48 (e.g., a hook) on the strap 46 may be attached to the corresponding attachment mechanism a loop) provided within the top layer 42 and 44. For example, the corresponding attachment mechanism may be an elastic loop sewn in to the top line (e.g., a seam of the inner panel) that allows the hook attachment mechanism to be selectively attached.

Figure 9:
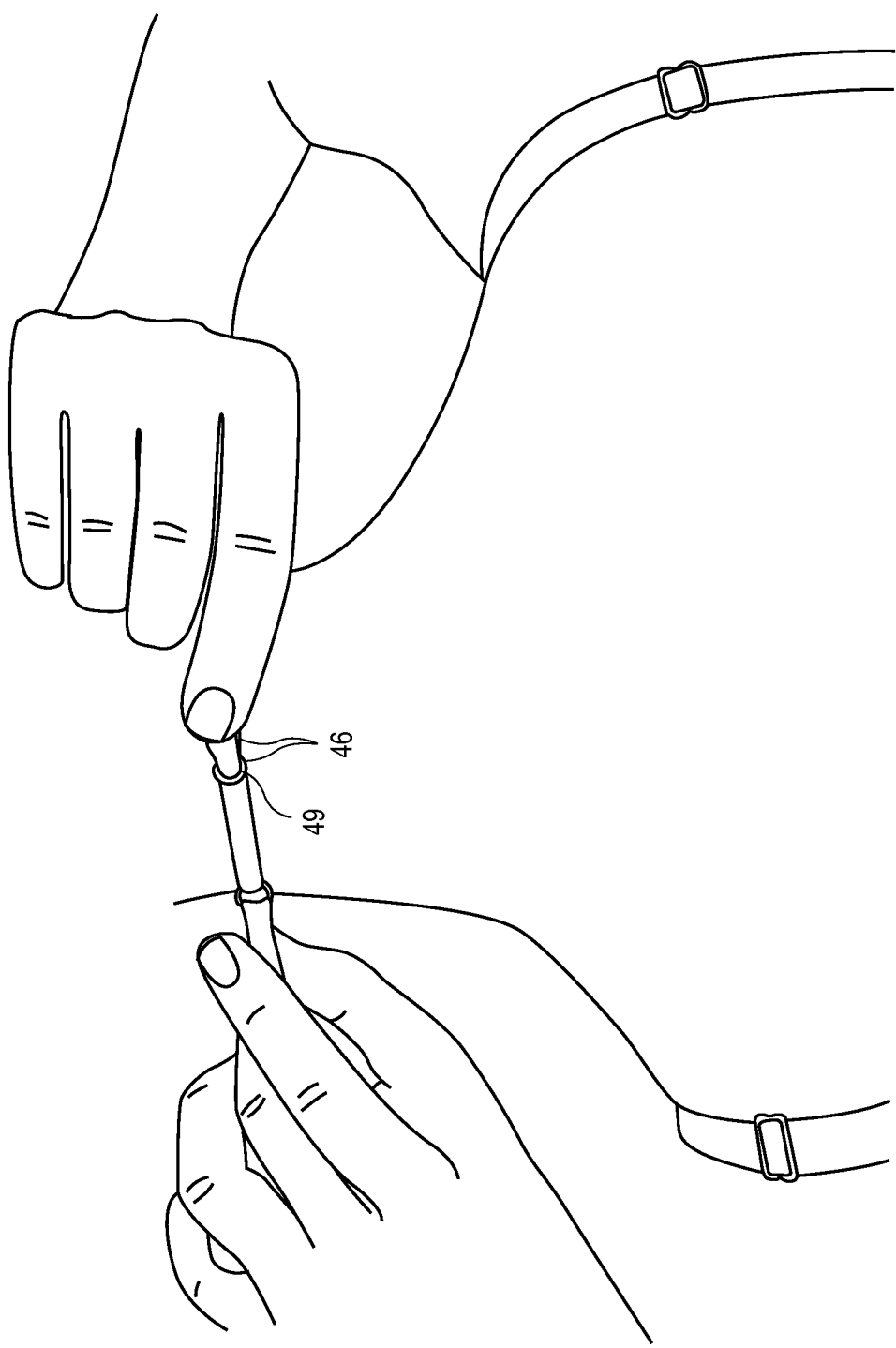
FIG. 9 depicts an exemplary garment in accordance with some embodiments of the invention.

FIG. 9 shows the manner in which the strap 46 encircles the neck of the wearer and a slide 49 is provided to adjust the length of the strap 46.

Figure 10:
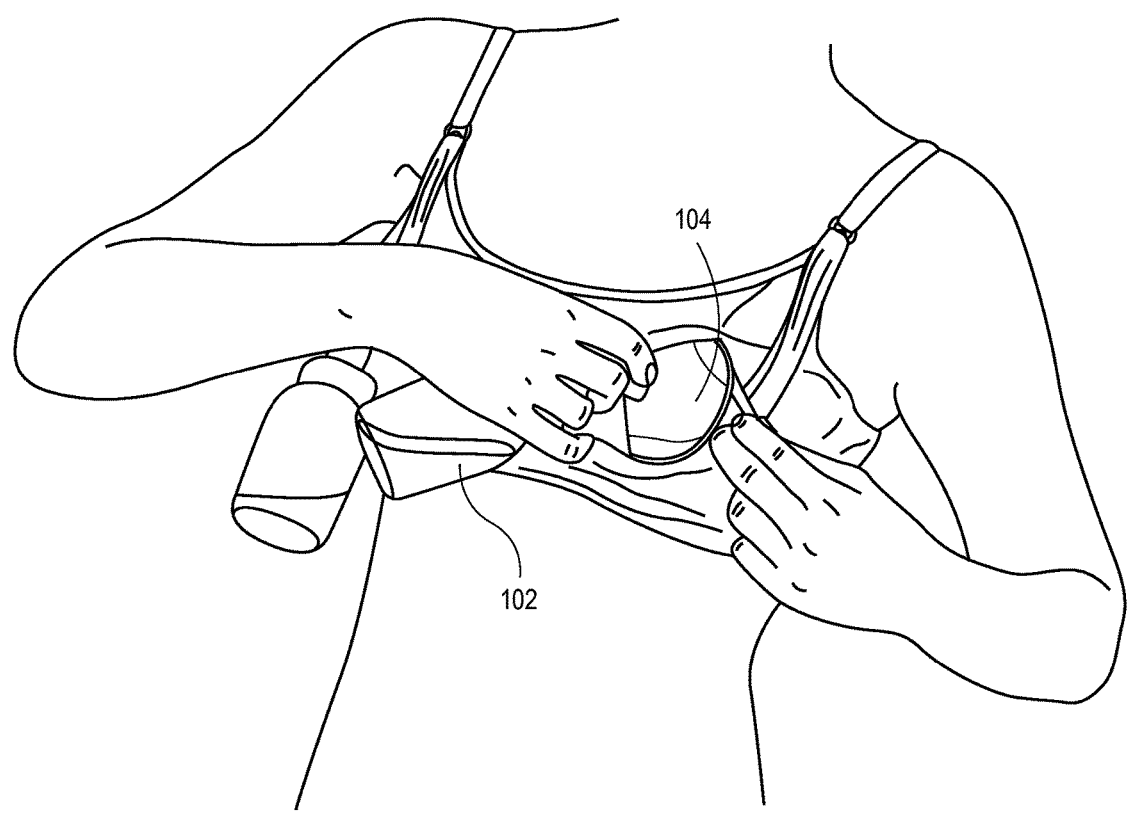
FIG. 10 depicts an exemplary garment in accordance with some embodiments of the invention.
Figure 11:
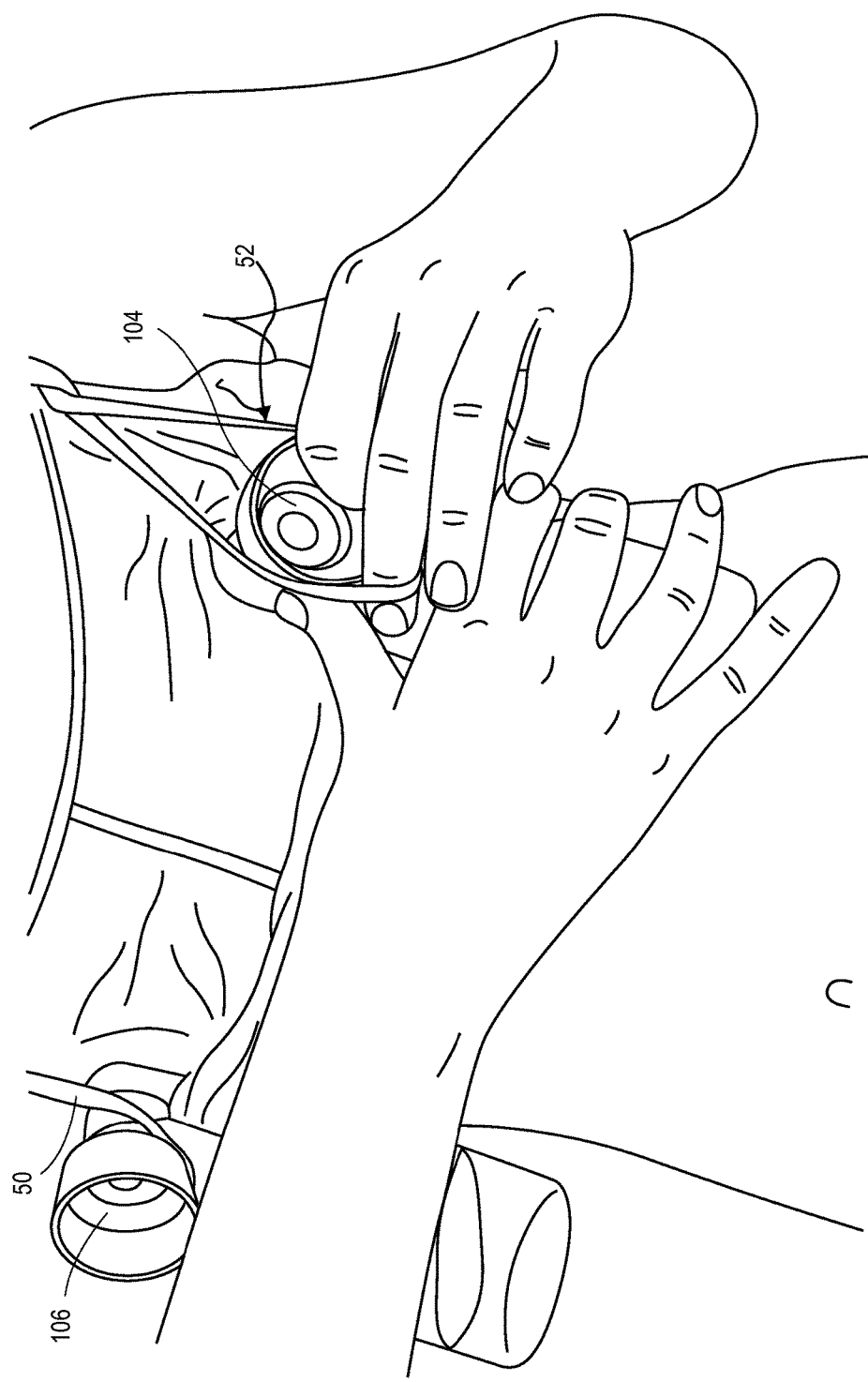
FIG. 11 depicts an exemplary garment in accordance with some embodiments of the invention.
Figure 12:
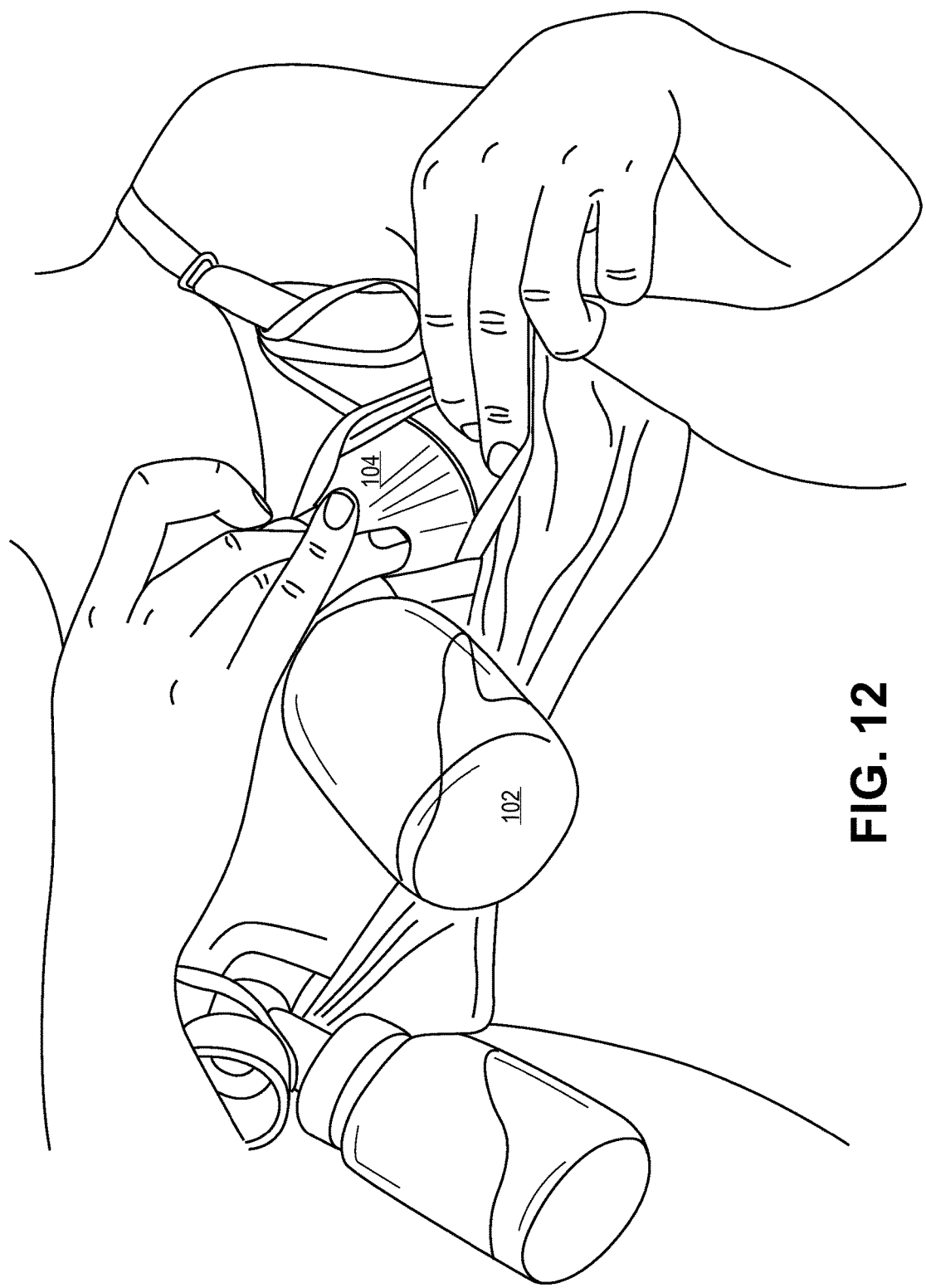
FIG. 12 depicts an exemplary garment in accordance with some embodiments of the invention.
Figure 14:
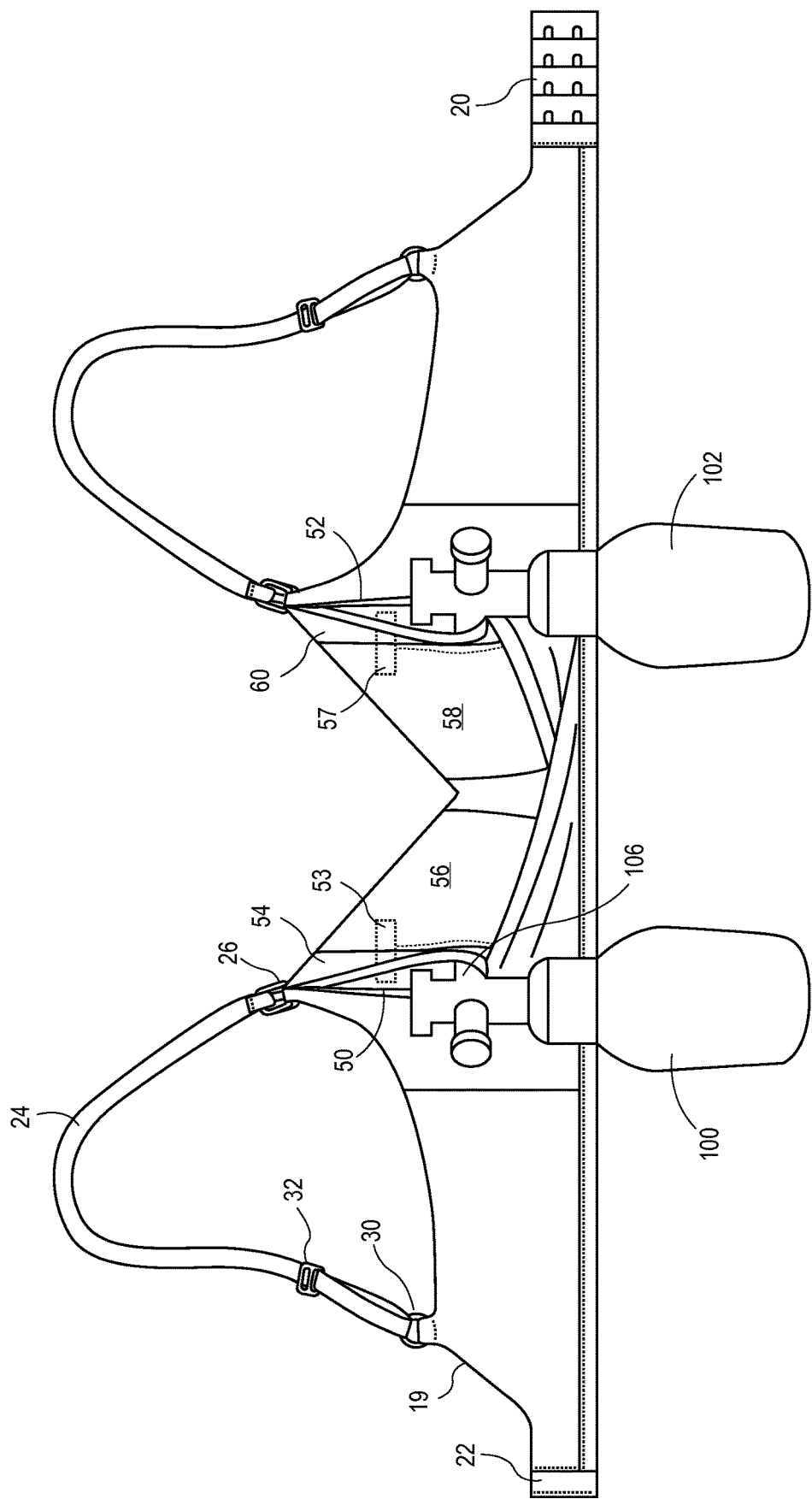
FIG. 14 depicts an exemplary garment in accordance with some embodiments of the invention.

FIGS. 10, 11, and 12 show the manner in which a breast shield may be inserted through an opening of the inner panel 19 of the garment 11. As illustrated in FIG. 11 and FIG. 14, for example, an elastic loop 52 may fit around the breast shield 104 and an elastic loop 50 may fit around breast shield of a breast pump body 106. The elastic loop 52 may fit around any part of the breast shield 106, any piece that connects the breast shield to the bottle (e.g., milk container), and/or the bottle itself. In some embodiments, multiple loops may be used. For example, one loop may fit around the shield or any connector used and the second loop might secure the bottle itself. In some embodiments, the loop may be formed from an elastic material and in other embodiments, a more rigid material may be used that has less stretch/elasticity. For example, a less elastic material or fabric may be used with a slider to allow for adjustment of length. The loops may be removable and attached to the garment using a hook or other attachment mechanism.

Figure 13:
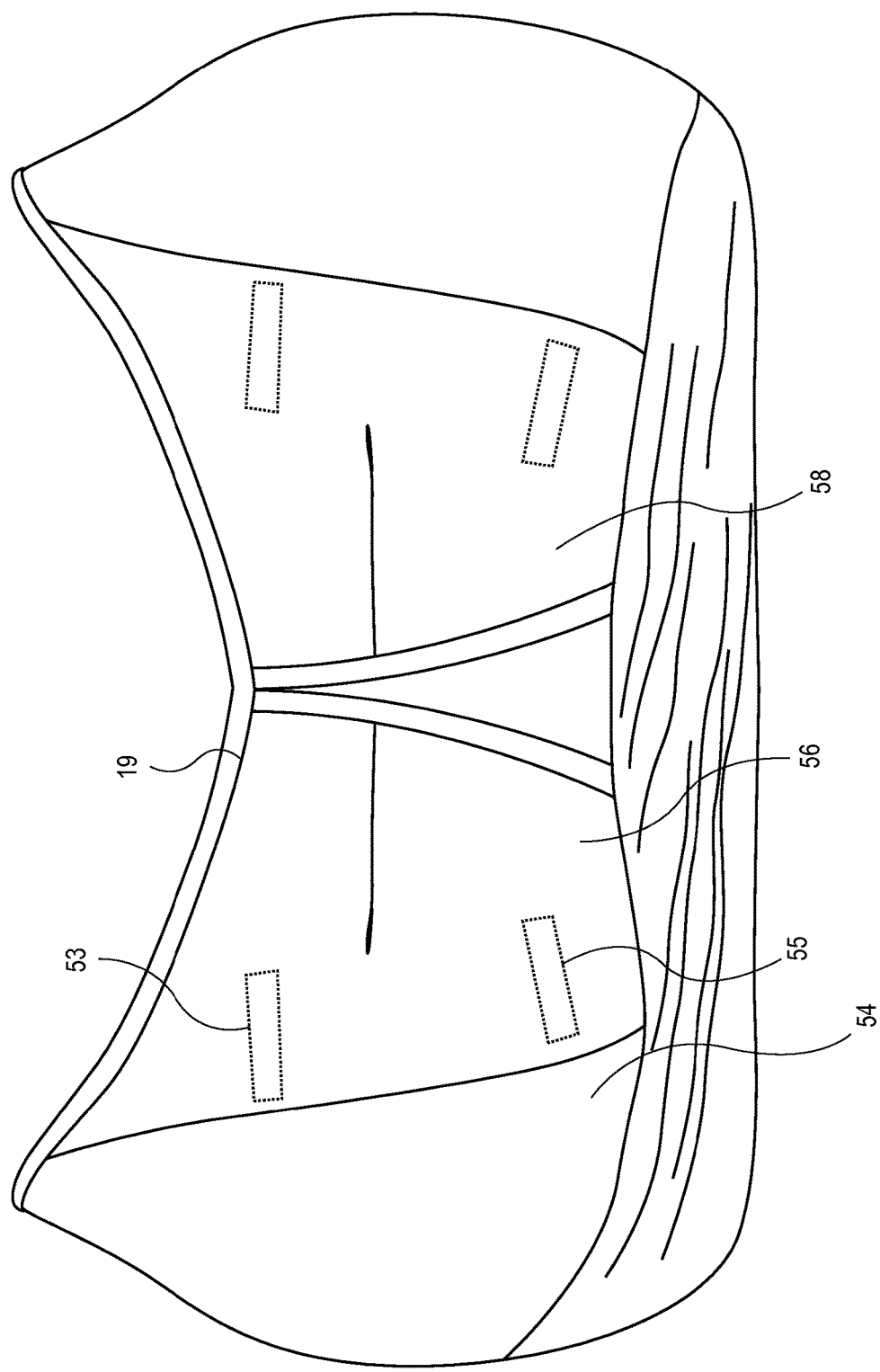
FIG. 13 depicts an exemplary garment in accordance with some embodiments of the invention.

FIG. 13 illustrates the inner panel 19, as well as the rectangular shaped stitching 53, 55 provided across a portion of the overlapping panels 54, 56 to fasten the overlapping layers together and create an opening.

It is noted that based upon the comfort level of the woman during breast milk pumping, the woman may choose to utilize the elastic loops 50, 52 to hook/fit around the breast shield, without the utilization of any of the straps 46, 66, 72. Alternatively, the woman might utilize straps 46, 66, or 72 without employing the elastic loops 50, 52. Furthermore, the woman might utilize both the elastic loops 50, 52 along with one of the straps 46, 66, or 72.

Figure 15:
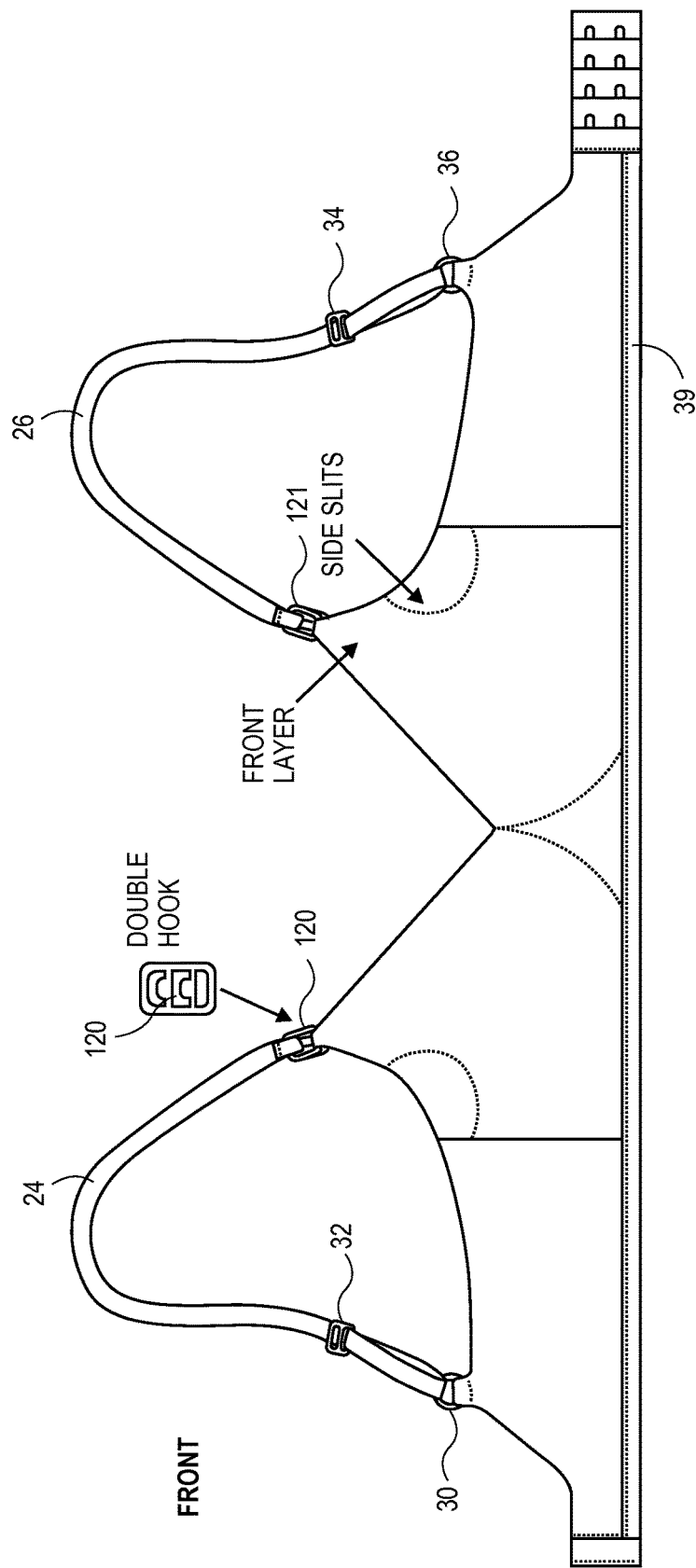
FIG. 15 depicts an exemplary garment in accordance with some embodiments of the invention.
Figure 16:
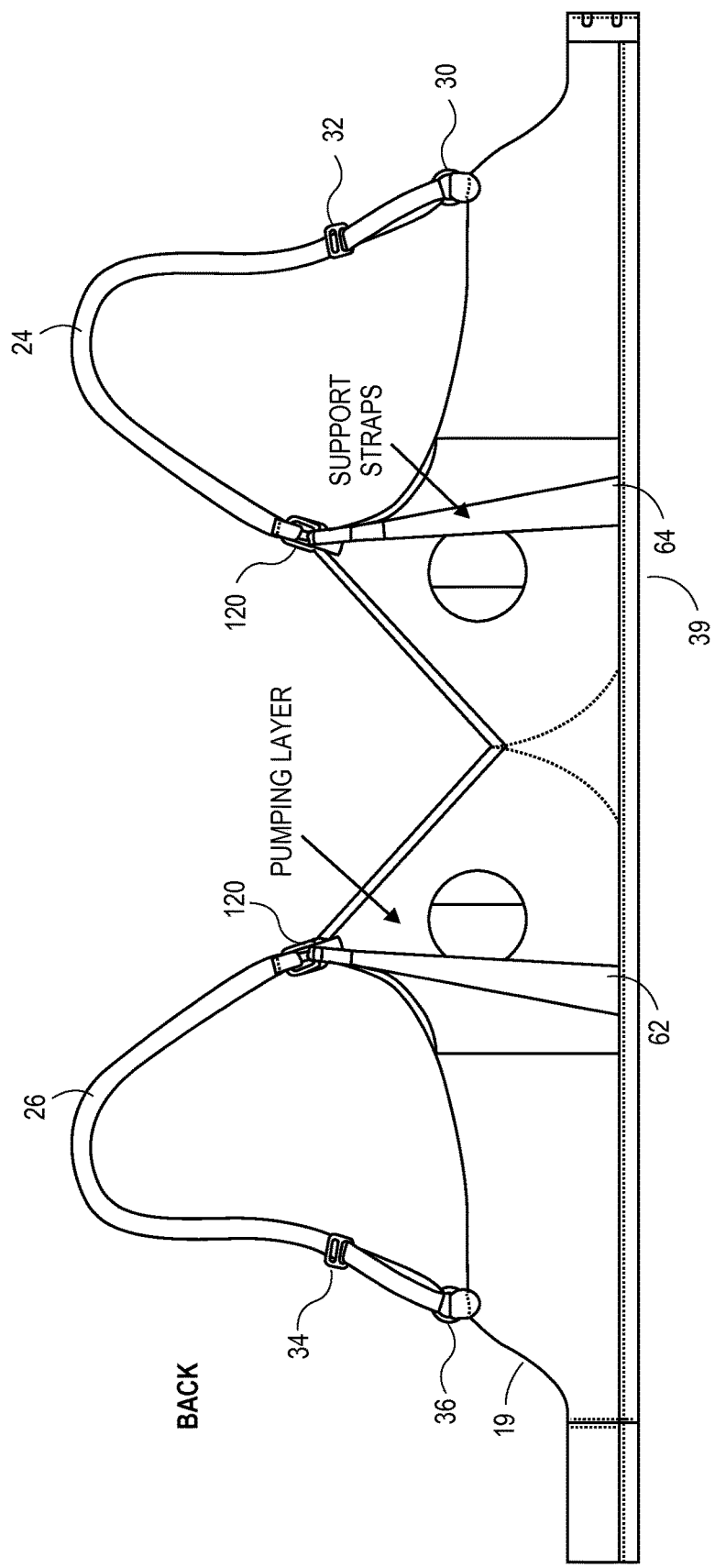
FIG. 16 depicts an exemplary garment in accordance with some embodiments of the invention.

FIGS. 15 and 16 depicts an exemplary garment in accordance with some embodiments of the invention. FIGS. 15 and 16 illustrate use of a double hook attachment mechanism. The first end of the double hook is sewn on the shoulder strap and the second end of the double hook is sewn to the fabric stay 62 and/or 64. The outer or exterior surface 17 hooks to the top catch of the double hook 120 and the pump, inner panel support hooks to the bottom catch of the double hook. The exterior surface 17 and inner panel 19 can be selectively hooked and unhooked from the catches of the double hooks.

The fabric stay 62 extends from the double hook 120 to the bottom 39 of the inner panel 19. Similarly, the fabric stay 64 extends from the double hook 120 to the bottom surface 39 of the pumping panel 19. The exterior surface 17 and inner panel 19 can be unhooked for nursing and reattached as desired. The fabric stays 62, 64 keep the shoulder straps secure on the shoulder, when the panels 16 and 18 are moved to allow for breast feeding. The inner panel 19 is provided with top rectangular shaped stitching 53 and a bottom rectangular shaped stitching 55 extending across a portion of the overlapping sections 54, 56 of the inner panel 19 to create an opening and provide support for a breast pump body. Similarly, a top rectangular stitching 57 and a bottom rectangular stitching 59 extend across a portion of the overlapping sections 58, 60 of the inner panel 19 to create an opening in and provide support for a breast pump body. FIGS. 15 and 16 have side slits on each side of inner panel 19. The side slits may be wide enough to fit one or more fingers to allow for massage of the area.

Figure 17:
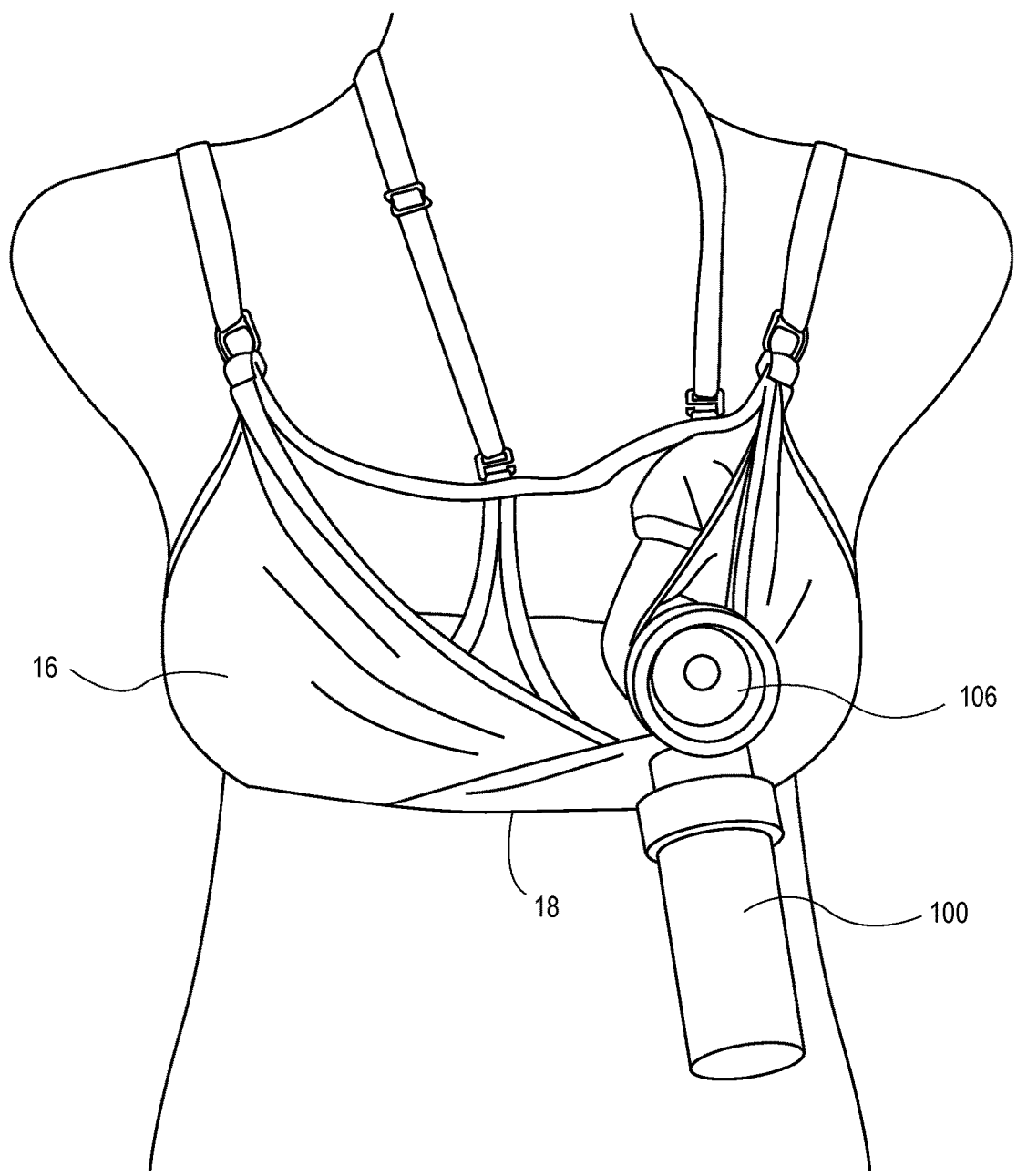
FIG. 17 depicts an exemplary garment in accordance with some embodiments of the invention.

FIG. 17 depicts an exemplary garment in accordance with some embodiments of the invention. FIG. 17 illustrates a strap attached to two corresponding attachment mechanisms on the garment 11 that are provided for selective positioning of the strap. As shown, the strap is positioned to provide support for the breast pump body 106 within an opening on a right facing side of the garment 11. The attachment mechanisms on the strap may be attached to various corresponding attachment mechanisms on the garment to support the breast pump body 106 as desired by the wearer. The positioning of the strap as shown is to provide support from the center and the left side (right facing side) of the garment 11 for the wearer.

Figure 18:
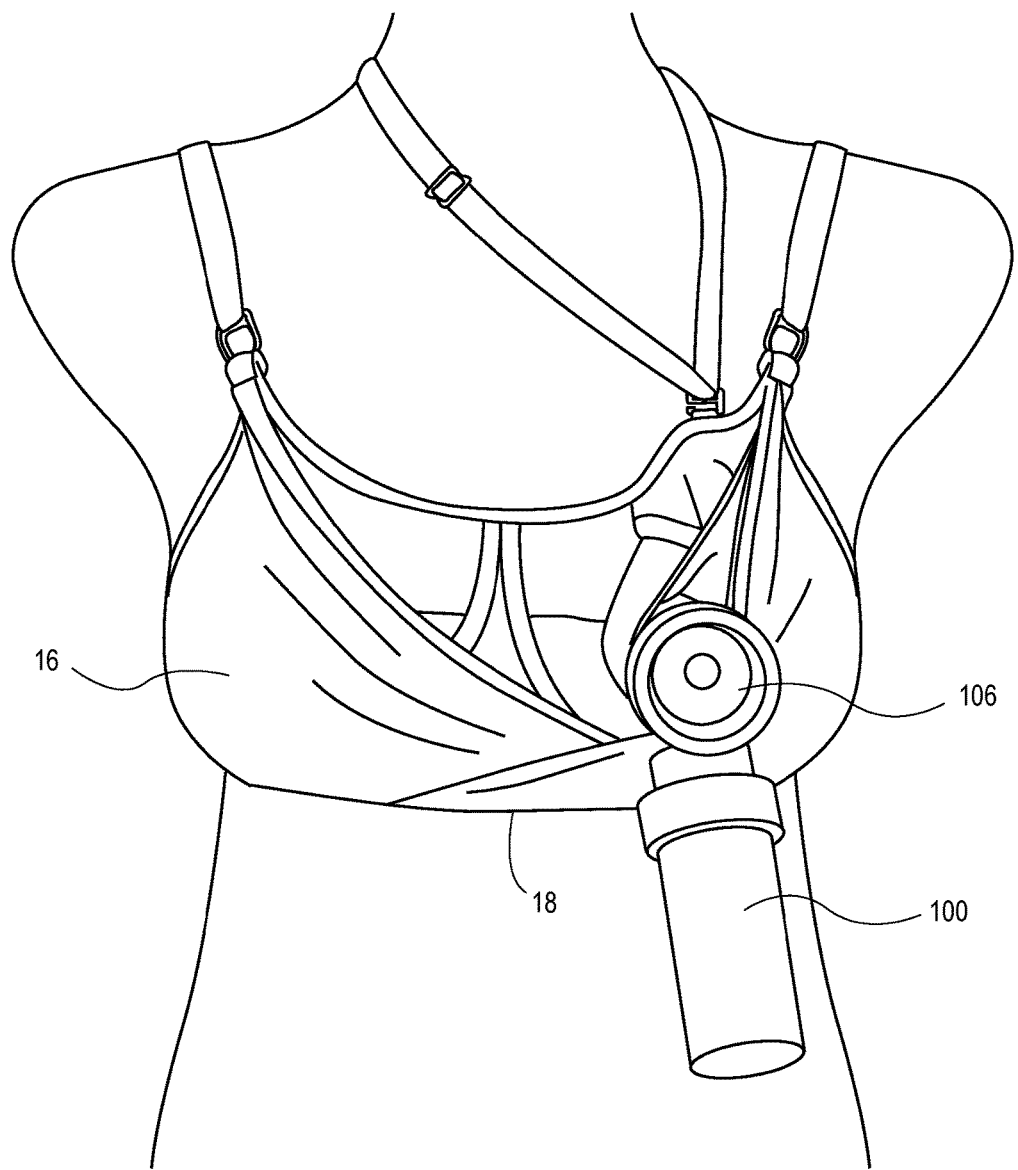
FIG. 18 depicts an exemplary garment in accordance with some embodiments of the invention.

FIG. 18 depicts an exemplary garment in accordance with some embodiments of the invention. FIG. 18 shows a strap attached to one attachment mechanism on the garment 11. The strap is positioned to provide further support for a breast pump body 106 within the opening on the right facing side of the garment 11. The positioning of the strap is to provide support from the left side (right facing side) of the garment 11 for the wearer.

Figure 19:
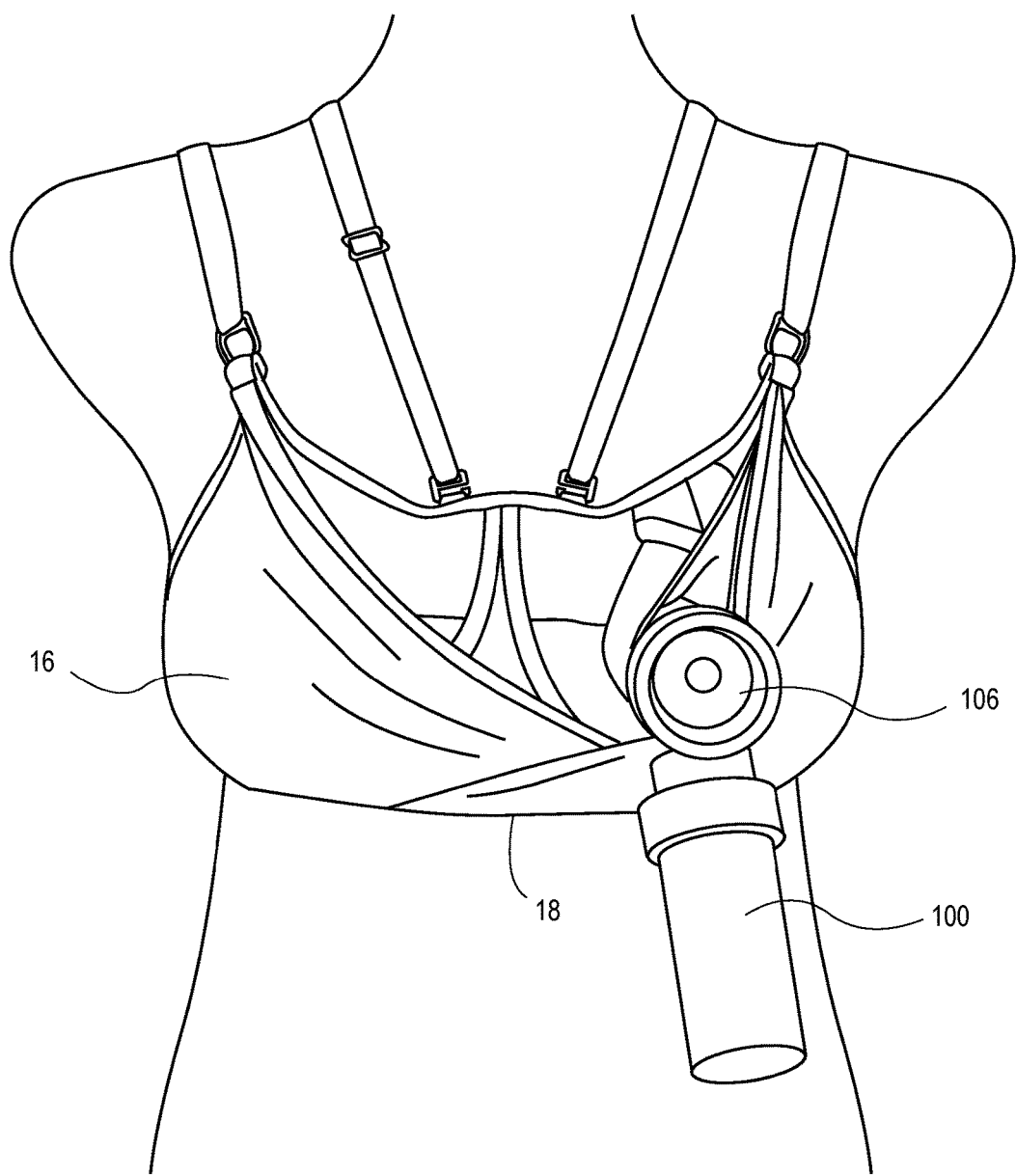
FIG. 19 depicts an exemplary garment in accordance with some embodiments of the invention.

FIG. 19 depicts an exemplary garment 11 in accordance with some embodiments of the invention. The strap is positioned using attachment mechanisms to provide more support from the center.

Figure 20:
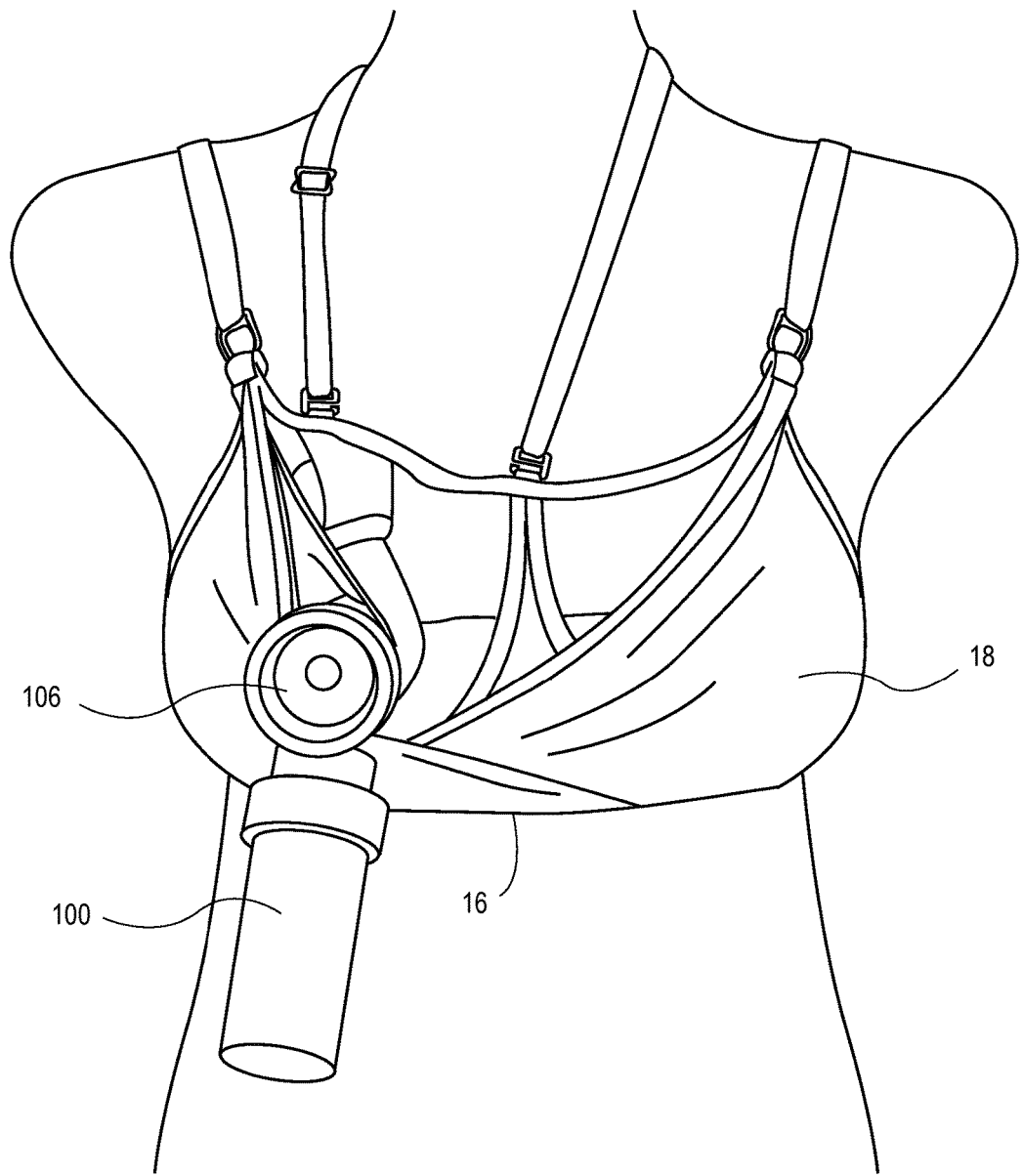
FIG. 20 depicts an exemplary garment in accordance with some embodiments of the invention.

FIG. 20 depicts an exemplary garment 11 in accordance with some embodiments of the invention. The strap is positioned to provide support from the center and the right side of the garment 11.

Figure 21:
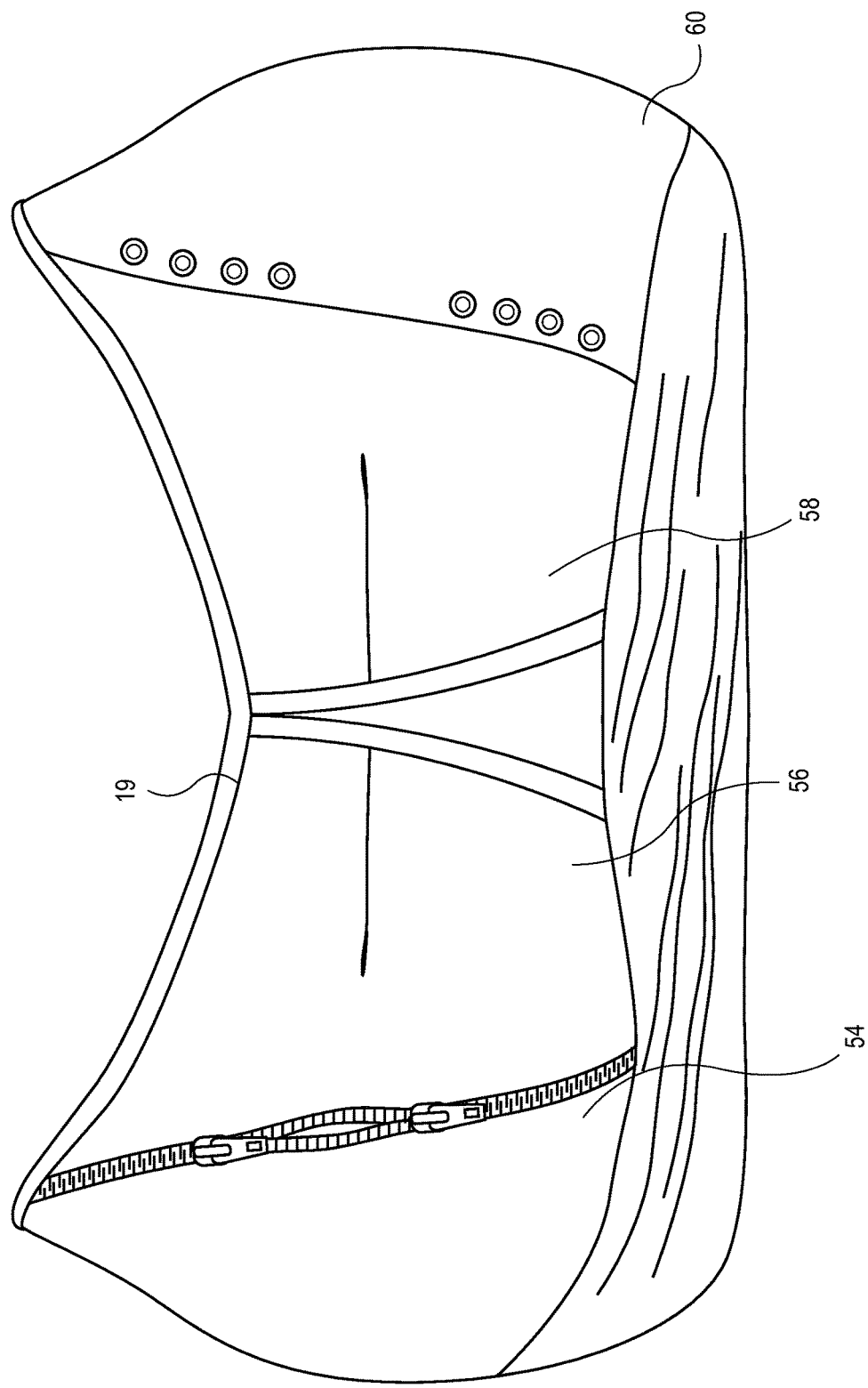
FIG. 21 depicts an exemplary garment in accordance with some embodiments of the invention.
Figure 22:
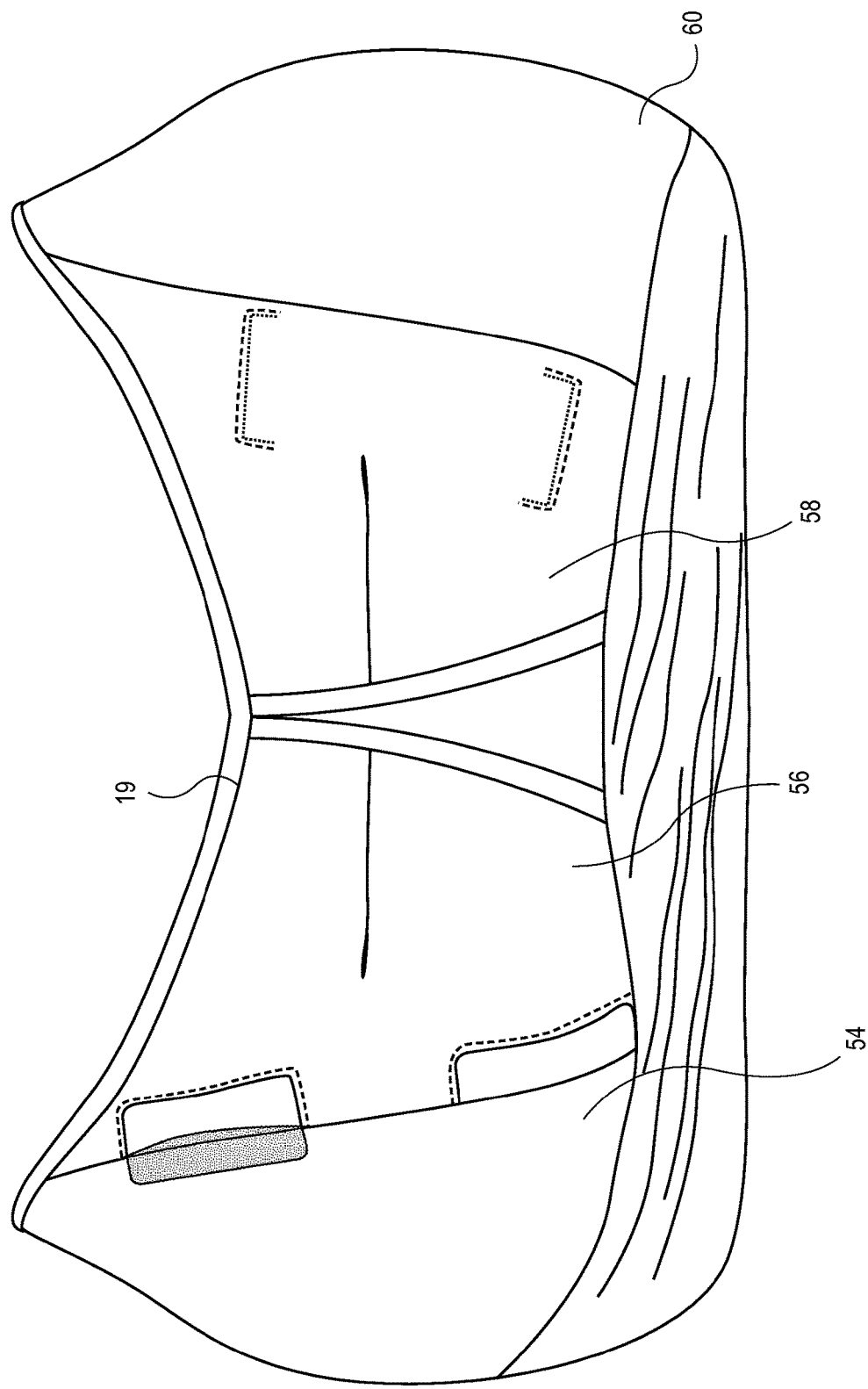
FIG. 22 depicts an exemplary garment in accordance with some embodiments of the invention.
Figure 23:
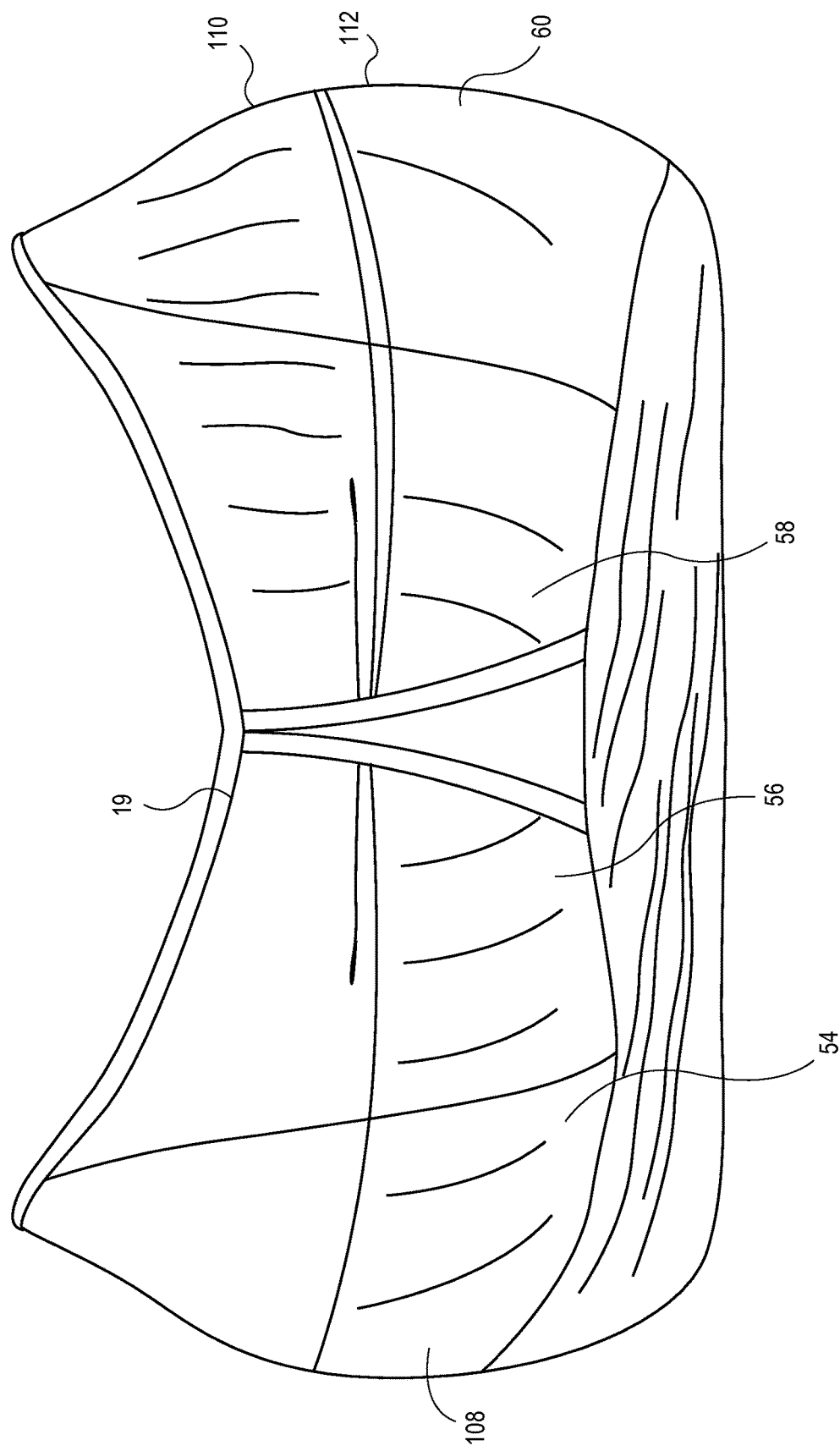
FIG. 23 depicts an exemplary garment in accordance with some embodiments of the invention.

FIGS. 21-23 illustrate various embodiments of a garment. For description purposes, each garment may be depicted with different fastening mechanisms and/or panels of material to describe features that may be incorporated into the garment. Those with skill in the art will recognize one or more features described may be incorporated into the garment. For example, zippers and/or snaps may be used to fasten panels of the garment 11, as described in FIG. 21, and both types of fasteners are not required.

FIG. 21 depicts an exemplary garment 11 in accordance with some embodiments of the invention. As shown in FIG. 21, a zipper is used to fasten panels (e.g., 54 and 56) and form an opening for at least a portion of the breast pump. Alternatively and/or in addition to use of other fasteners, snaps may be used to fasten panels (e.g., 58 and 60) together to form an opening for at least a portion of the breast pump. The snaps may be snapped or unsnapped to adjust the size of the opening between panels. Stitching between the panels may or may not be used with other fasteners to fasten panels together. The fasteners may aid in further securing the panels together and keep the breast shield in place.

FIG. 22 depicts an exemplary garment 11 in accordance with some embodiments of the invention. As shown in FIG. 22, VELCRO fasteners may be used to fasten panels together (e.g., panels 54 and 56). Stitched fasteners between panels (e.g., panels 58 and 60) may have elastic pieces stitched in to one or more of the edges of the stitching. The elastic pieces may provide additional support for keeping portions of the breast pump in place. The stitching may not have a rectangular shape as shown. One or more portions of the panels 58 and 60 may be stitched to fasten the panels together and create an opening.

FIG. 23 depicts an exemplary garment in accordance with some embodiments of the invention. Layers of material (e.g., 108, 110, and 112) may be provided under or over panels (e.g., 54, 56, 58, and 60) of the inner panel to provide additional support. For example, a layer of material 108 may be placed over at least a portion of panels 54 and 56 as shown and provide support for at least a portion of the breast pump. In other embodiments, the material 108 may be placed behind panels 54 and 56.

Figure 24:
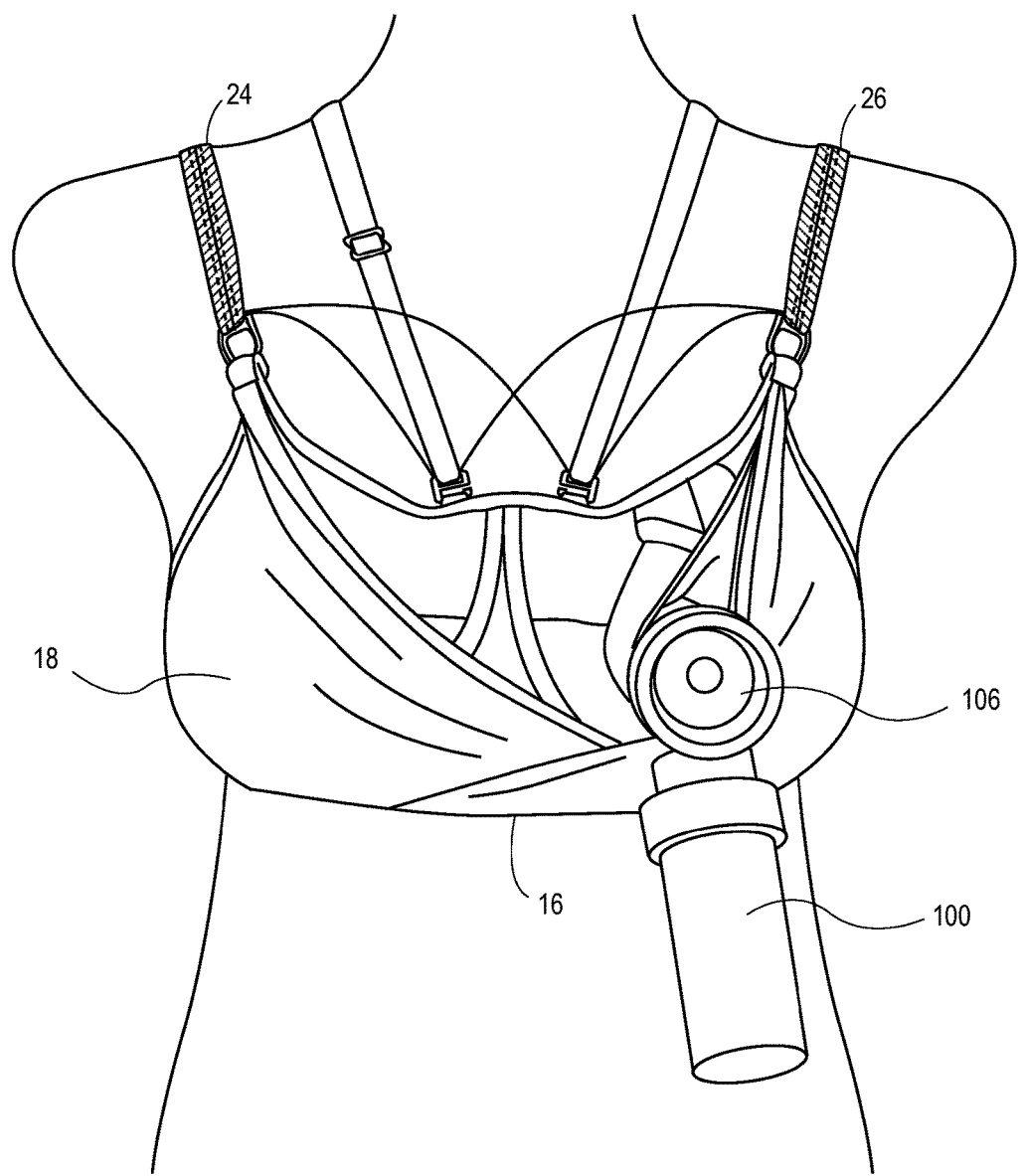
FIG. 24 depicts an exemplary garment in accordance with some embodiments of the invention.

FIG. 24 depicts an exemplary garment 11 in accordance with some embodiments of the invention. FIG. 24 illustrates use of a channel or pocket within the straps (e.g., 24 and 26) of the garment. The channel or pocket of the straps may house one or more cords, such as an elastic cord covered in a fabric, that can be extracted and/or expanded and then attached to another portion of the garment as shown. The cord may be retracted and/or recoiled when not in use. The cord may have attachment mechanisms to allow for attachment to other portions of the garment. The cord may have sliders to allow for adjustment of the length.

Figure 25:
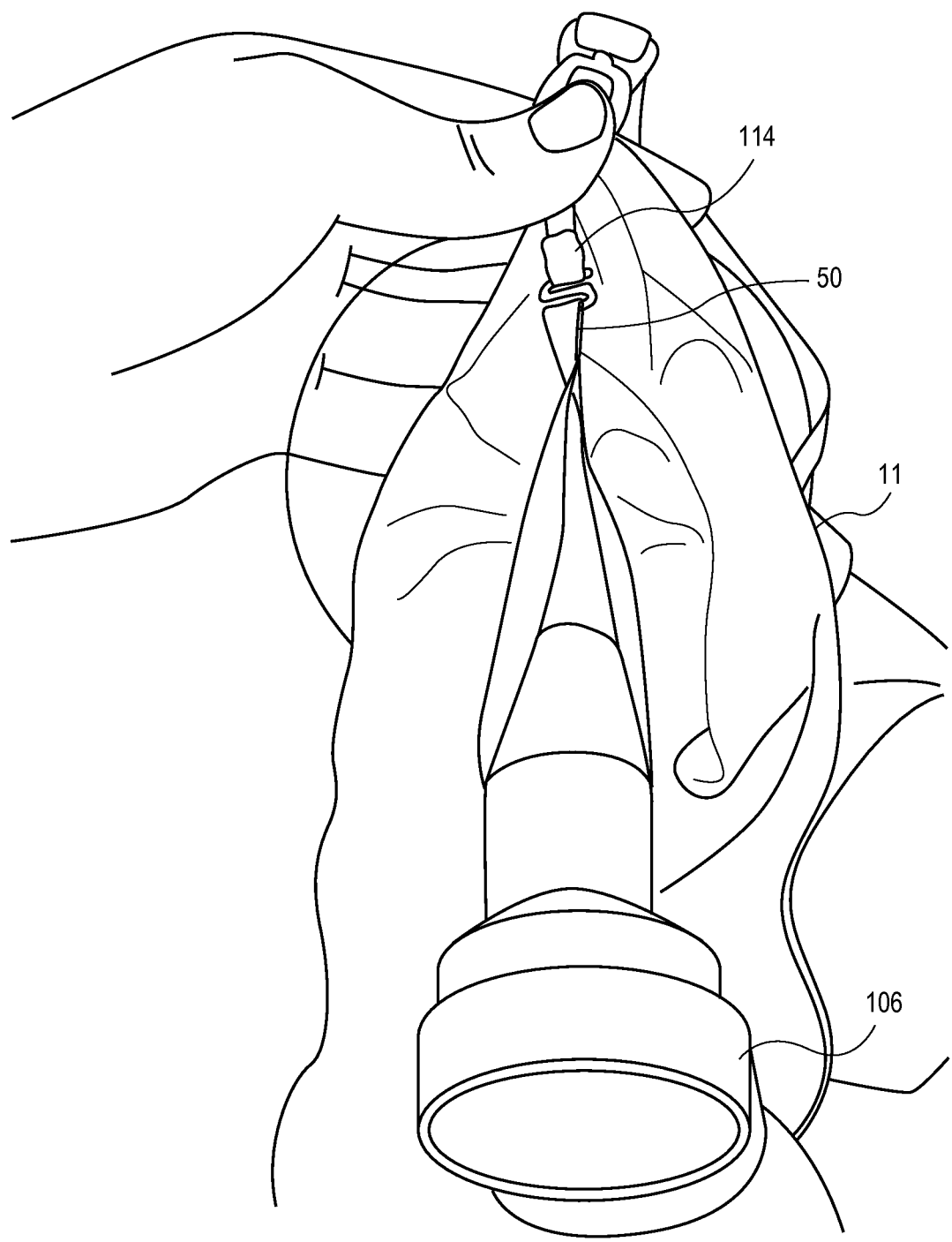
FIG. 25 depicts an exemplary garment in accordance with some embodiments of the invention.
Figure 26:
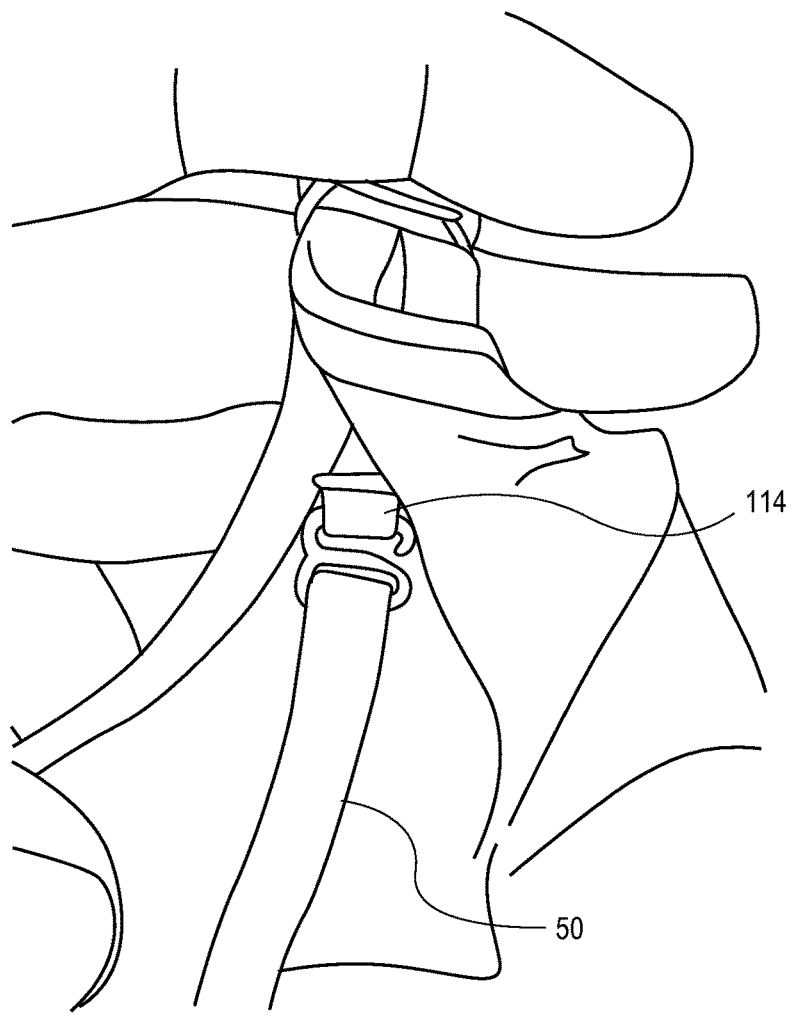
FIG. 26 depicts an exemplary garment in accordance with some embodiments of the invention.
Figure 27:
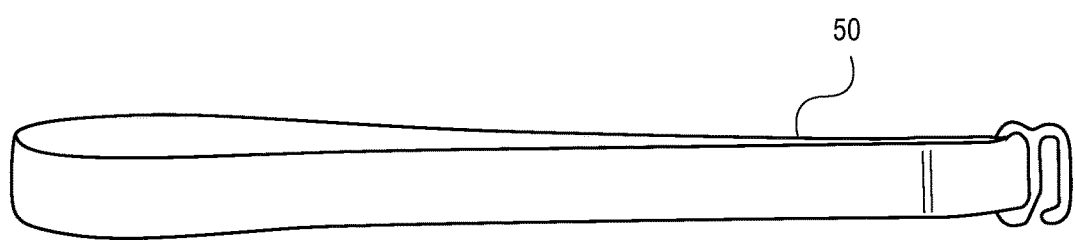
FIG. 27 depicts an exemplary garment in accordance with some embodiments of the invention.

FIGS. 25, 26, and 27 depicts an exemplary garment 11 in accordance with some embodiments of the invention with a detachable elastic loop 50. As shown, elastic loop 50 (and loop 52) may be selectively attached and/or detached from attachment mechanism 114 (e.g. a hook) on the garment.

While the preferred embodiments have been shown and described, it will be understood that there is no intent to limit the invention by such disclosure, but rather, is intended to cover all modifications and alternate constructions falling within the spirit and scope of the invention.

What is claimed:

1. A garment, comprising:
    an inner panel including a first covering configured to cover a first breast of a wearer and a second covering configured to cover a second breast of the wearer, at least one of the first covering or the second covering including a first layer of material coupled to a second layer of material such that a portion of the first layer of material overlaps a portion of the second layer of material and an opening is defined between the overlapping portions of the first layer of material and the second layer of material, the at least one of the first covering or the second covering configured to provide support during milk expression for at least one of the wearer's breast and a portion of a breast pump body when the breast pump is inserted through the opening; and an exterior panel including a first panel of material and a second panel of material, the first panel of material overlaps at least a portion of the second panel of material, the first panel of material configured to be moved to expose the overlapped portion of the second panel of material, the second panel of material overlaps at least a portion of the first covering of the inner panel and at least a portion of the second covering of the inner panel, at least one of the first panel of material or the second panel of material configured to be moved to expose the at least one of the first covering or the second covering of the inner panel.

2. The garment of claim 1, wherein when the breast pump body is inserted through the opening, the portion of the breast pump is supported by the first layer of material and the second layer of material.

3. The garment of claim 1, wherein, when the first panel of material and the second panel of material are moved to expose the at least one of the first covering or the second covering of the inner panel, the first panel of material and the second panel of material are configured to provide support for the portion of the breast pump body inserted through the opening.

4. The garment of claim 1, wherein the first layer of material and the second layer of material each include a fabric with elasticity.

5. The garment of claim 1, wherein the opening is a first opening, the at least one of the first covering and the second covering is the first covering, and the second covering includes a third layer of material coupled to a fourth layer of material such that a portion of the third layer of material overlaps a portion of the fourth layer of material and a second opening is defined between the overlapping portions of the third layer of material and the fourth layer of material.

6. The garment of claim 1, wherein the inner panel has a bottom edge, the first layer of material has a first edge defining a first portion of the opening, the second layer of material has a second edge defining a second portion of the opening, and the first layer of material and the second layer of material are attached to the inner panel such that the first edge and the second edge are disposed substantially perpendicular to the bottom edge of the inner panel.

7. The garment of claim 1, further comprising at least one shoulder strap and a neck strap, the at least one shoulder strap attached to the inner panel, the neck strap selectively attachable to the inner panel and configured to fit around the wearer's neck and provide support for the portion of the breast pump body.

8. The garment of claim 1, further comprising at least one loop of material selectively attachable to the garment and configured to fit around a portion of the breast pump and secure the breast pump in place within the opening.

9. The garment of claim 1, wherein the portion of the breast pump body is a breast shield.

10. The garment of claim 1, wherein the first panel of material crosses over the second panel of material such that the inner panel is substantially covered by the exterior panel.

11. The garment of claim 1, wherein the first layer of material and the second layer of material are fastened together with at least one of bar tack stitching, a rectangular shaped stitching, a hook and loop fastener, a zipper, stitching with elastic to provide additional support, and at least one snap.

12. The garment of claim 1, further comprising a shoulder strap having a retractable cord, the shoulder strap being selectively attachable to the inner panel to provide support.

13. The garment of claim 1, further comprising a shoulder strap having a double hook configured to allow for selective attachment of the inner panel and the exterior panel.

14. A garment comprising:
an inner panel including a first covering configured to cover a first breast of a wearer and a second covering configured to cover a second breast of the wearer, at least one of the first covering or the second covering defining a first opening configured to receive a portion of a breast pump therethrough;

an exterior panel including a first panel of material and a second panel of material, the first panel of material overlaps at least a portion of the second panel of material, and the first panel of material is configured to be moved to expose the overlapped portion of the second panel of material, the second panel of material overlapping at least a portion of the first covering and at least a portion of the second covering, at least one of the first panel of material or the second panel of material configured to be moved to expose the first opening; and at least one loop of material selectively attachable to the inner panel, the at least one loop of material defining a second opening configured to receive therethrough at least a portion of the breast pump when the breast pump is disposed within the first opening of the inner panel.

15. The garment of claim 14, wherein the at least one loop is an elastic loop sewn into at least one of the panel and a shoulder strap selectively attachable to the panel.

16. The garment of claim 14, wherein the at least one loop is an elastic loop selectively attachable to the inner panel with an attachment mechanism.

17. The garment of claim 14, wherein the at least one loop is configured to encircle a portion of the breast pump and secure the breast pump at an angle against the wearer.

18. A garment comprising:
at least one panel of material to fit around a wearer's chest, the at least one panel including a front portion and a back portion, the front portion configured to cover at least one breast of the wearer;

a first shoulder strap couplable to the front portion of the at least one panel of material at a first location on the front portion;

a second shoulder strap couplable to the front portion of the at least one panel of material at a second location on the front portion;

a support strap couplable to the front portion of the at least one panel of material;

an attachment mechanism coupled to the support strap; and a plurality of attachment mechanisms disposed on the front portion of the at least one panel of material between the first location and the second location, the plurality of attachment mechanisms on the front portion of the at least one panel of material each configured to selectively be coupled to the attachment mechanism on the support strap, the plurality of attachment mechanisms on the front portion of the at least one panel of material being disposed at spaced positions on the front portion of the at least one panel of material to provide a plurality of selectable attachment positions for attaching the support strap to the front portion of the at least one panel of material.

19. The garment of claim 18, wherein the support strap is a neck strap and the attachment mechanism on the support strap is a first strap attachment mechanism, the garment further comprising:
a second strap attachment mechanism coupled to the support strap,
a first attachment mechanism from the plurality of attachment mechanisms disposed at a center location of the at least one panel and a second attachment mechanism from the plurality of attachment mechanisms is disposed at one of a left side location and a right side location of the at least one panel such that, when the first strap attachment mechanism is coupled to the first attachment mechanism of the at least one panel and the second strap attachment mechanism is coupled to the second attachment mechanism of the at least one panel, the support strap is configured to support at least a portion of a breast pump body on a side of the garment corresponding with the one of the left side location and the right side location of the at least one panel.

20. The garment of claim 18, wherein the attachment mechanism of the support strap is a hook and each attachment mechanism from the plurality of attachment mechanisms includes a loop configured to selectively receive the hook.

21. The garment of claim 14, wherein at least one of the first covering or the second covering includes a first layer of material and a second layer of material coupled to the first layer of material such that a portion of the first layer of material overlaps a portion of the second layer of material and the first opening is defined between the overlapping portions of the first layer of material and the second layer of material, the first layer of material and the second layer of material collectively configured to provide support during milk expression for at least one of the wearer's breast and the portion of the breast pump body when inserted through the opening.

22. The garment of claim 18, wherein the at least one panel of material is configured to support a portion of a breast pump body when the breast pump body is held adjacent to one of a wearer's breast during milk expression performed with the breast pump body.

23. The garment of claim 18, wherein the at least one panel of material includes at least one covering configured to cover a breast of a wearer and including a first layer of material coupled to a second layer of material such that a portion of the first layer of material overlaps a portion of the second layer of material and an opening is defined between the overlapping portions of the first layer of material and the second layer of material, the at least one covering configured to provide support during milk expression for at least one of the wearer's breast and a portion of the breast pump body when the breast pump body is inserted through the opening.

24. The garment of claim 1, wherein the first panel of material further overlaps at least a portion of the first covering of the inner panel and at least a portion of the second covering of the inner panel.

* * * * *

UNITED STATES PATENT AND TRADEMARK OFFICE
CERTIFICATE OF CORRECTION

PATENT NO. : 9,872,524 B2  
APPLICATION NO. : 14/172826  
DATED : January 23, 2018  
INVENTOR(S) : Debra Abbaszadeh Page 1 of 1

It is certified that error appears in the above-identified patent and that said Letters Patent is hereby corrected as shown below:

In the Specification

Column 7, Line 41: "2E" should be --2B--,

Column 8, Line 33: "mechanism a loop)" should be --mechanism (e.g., a loop)--.

Signed and Sealed this
Twenty-second Day of May, 2018

Andrei Iancu
*Director of the United States Patent and Trademark Office*